United States Patent
Butterwick et al.

(10) Patent No.: US 12,033,757 B2
(45) Date of Patent: Jul. 9, 2024

(54) SYSTEMS AND METHODS FOR MAINTAINING OPTIMAL GROWTH IN ANIMALS

(71) Applicant: MARS, INCORPORATED, McLean, VA (US)

(72) Inventors: Richard Fulton Butterwick, Leicestershire (GB); Matthew James Harrison, Leicestershire (GB); Carina Salt, Leicestershire (GB); Sophie Bradley, Leicestershire (GB); Penelope J. Morris, Leicestershire (GB)

(73) Assignee: MARS, INCORPORATED, McLean, VA (US)

( * ) Notice: Subject to any disclaimer, the term of this patent is extended or adjusted under 35 U.S.C. 154(b) by 0 days.

(21) Appl. No.: 17/887,304

(22) Filed: Aug. 12, 2022

(65) Prior Publication Data
US 2023/0042191 A1 Feb. 9, 2023

Related U.S. Application Data

(63) Continuation of application No. 16/476,438, filed as application No. PCT/US2018/012935 on Jan. 9, 2018, now abandoned.
(Continued)

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/1075* (2013.01); *A61B 5/7275* (2013.01); *G16H 20/30* (2018.01);
(Continued)

(58) Field of Classification Search
None
See application file for complete search history.

(56) References Cited

U.S. PATENT DOCUMENTS

| 8,815,279 B2 | 8/2014 | Singhal et al. |
| 2003/0014279 A1 | 1/2003 | Roman et al. |

(Continued)

FOREIGN PATENT DOCUMENTS

WO  WO 2016/083501 A1  6/2016

OTHER PUBLICATIONS

Demler, Impact of New Variables on Discrimination of Risk Prediction Models, 2012, Boston University Graduate School of Arts and Sciences Dissertation (Year: 2012).*

(Continued)

*Primary Examiner* — Karen A Hranek
(74) *Attorney, Agent, or Firm* — Baker Botts L.L.P.

(57) ABSTRACT

A software application platform which provides a user with the ability to receive customized information relating to an animal's health and/or optimal growth as displayed on a graphical user interface. Specifically, a user may input data (and the system may receive said input data), for example, an animal specific biomarker, and subsequently receive identification relating to a specific subgroup of individual animal(s) who are at risk for growth abnormalities, and further receive information, data, and customized recommendations and/or intervention steps for the specific at risk animal relating to the animal's health, growth abnormality, or similar feature based on an analysis and determination of the biomarker as compared to a reference database.

24 Claims, 12 Drawing Sheets

Related U.S. Application Data

(60) Provisional application No. 62/444,079, filed on Jan. 9, 2017.

(51) Int. Cl.
| | |
|---|---|
| *A61B 5/107* | (2006.01) |
| *G16H 20/30* | (2018.01) |
| *G16H 20/60* | (2018.01) |
| *G16H 50/20* | (2018.01) |

(52) U.S. Cl.
CPC .............. *G16H 20/60* (2018.01); *G16H 50/20* (2018.01); *A61B 2503/40* (2013.01)

(56) References Cited

U.S. PATENT DOCUMENTS

| | | |
|---|---|---|
| 2006/0036419 A1 | 2/2006 | Cook et al. |
| 2009/0123951 A1 | 5/2009 | Kim et al. |
| 2011/0125062 A1 | 5/2011 | Mulder |
| 2015/0154887 A1 | 6/2015 | Spivey-Krobath |
| 2016/0012748 A1 | 1/2016 | Donavon |
| 2016/0042038 A1 | 2/2016 | Schumacher et al. |
| 2016/0155347 A1 | 6/2016 | Spivey-Krobath et al. |
| 2016/0165853 A1 | 6/2016 | Goldfain |
| 2016/0246934 A1 | 8/2016 | Dunlop |
| 2016/0360733 A1* | 12/2016 | Triener .................. G01G 17/08 |
| 2018/0078214 A1 | 3/2018 | Flanagan et al. |
| 2018/0132519 A1 | 5/2018 | Solly |

OTHER PUBLICATIONS

Xanthakis, Assessting Methods for Inclusion of New Disease Markers into Risk Prediction Models, 2012, Boston University Graduate School of Arts and Sciences Dissertation (Year: 2012).*

Nagy et al., Percentile reference values for anthropometric body compsition indices in European children from the IDEFICS study, 2014, International Journal of Obesity 38 (Year: 2014).*

Antunes, Human Growth, Biological Maturation, Motor Performance and Contextual Factors in Madeira Children, Sep. 2014, Universidade da Madeira Doctoral Thesis (Year: 2014).*

Alexander et al., Effects of neutering on food intake, body weight and body composition in growing female kittens, 2011, British Journal of Nutrition (Year: 2011).*

U.S. Appl. No. 16/476,438 (US 2020/0058405), filed Jul. 8, 2019 (Feb. 20, 2020).

U.S. Appl. No. 16/476,438, filed Sep. 9, 2022 Non-Final Office Action.

U.S. Appl. No. 16/476,438, filed Aug. 12, 2022 Request for Continued Examination (RCE) and Response to Final Office Action.

U.S. Appl. No. 16/476,438, filed May 13, 2022 Final Office Action.

U.S. Appl. No. 16/476,438, filed Feb. 7, 2022 Response to Non-Final Office Action.

U.S. Appl. No. 16/476,438, filed Nov. 17, 2021 Non-Final Office Action.

Demmelmair, et al., "Long-term consequences of early nutrition", Early Human Development (Aug. 2006) 82, 567-574.

Diez, et al., "Weight Loss in Obese Dogs: Evaluation of a High-Protein, Low-Carbohydrate Diet", The Journal of Nutri. American Society for Nutrition, US, vol. 132, No. 6, Suppl. 02, (Jun. 2002), pp. 1685S-1687S.

Emdadi, et al., "Standardized Percentile Curves of Body Mass Index of Northeast Iranian Children Aged 25 to 60 Months", Iranian Journal of Pediatrics, 21(1):88-94 (2011).

International Search Report dated May 14, 2018, in International Application No. PCT/US2018/012935.

Koletzko, et al., "Symposium on 'Metabolic flexibility in animal and human nutrition" Session I: Early nutrition programming, life performance and cognitive function, Early nutrition programming of long-term health, Proceedings of the Nutrition Society (Aug. 2012), 71, 371-378.

Laflamme, "Development and Validation of a Body Condition Score System for Dogs", Canine Practice, vol. 22, No. 4, pp. 10-15, Jul./Aug. 1997.

Leclerc, et al., "Higher Neonatal Growth Rate and Body Condition Score at 7 Months are Predictive Factors of Obesity in Adult Female Beagle Dogs", BMC Veterinary Research, vol. 13, No. 1, (Apr. 2017) pp. 1-13.

Rigby, et al., "Automatic smoothing parameter selection in GAMLSS with an application to centile estimation", Statistical Methods in Medical Research, 23(4):318-332 (2014).

Rigby, et al., "Smooth centile curves for skew and kurtotic data modelled using the Box-Cox power exponential distribution", Statistics in Medicine, 23(19):3053-3076 (2004).

Stettler, et al., Weight Gain in the First Week of Life and Overweight in Adulthood: A Cohort Study of European American Subjects Fed Infant Formula, Circulation, vol. 111, No. 15 (Apr. 2005), pp. 1897-1903.

Urlacher, "Growing Up Shuar: Life History Tradeoffs and Energy Allocation in the Context of Physical Growth Among an Indigenous Amazonian Population", dissertation for the Department of Human Evolutionary Biology of Harvard University (2016).

Weber, et al., "A High-Protein, High-Fiber Diet Designed for Weight Loss Improves Satiety in Dogs", J. Vet. Intern. Med., vol. 21, No. 6, (Nov. 2007), pp. 1203-1208.

* cited by examiner

SYSTEMS AND METHODS FOR MAINTAINING OPTIMAL GROWTH IN ANIMALS

CROSS-REFERENCE TO RELATED APPLICATION

This application is a continuation of U.S. patent application Ser. No. 16/476,438, filed on Jul. 8, 2019, which is a U.S. National Stage Patent Application under 35 U.S.C. § 371 of International Application No. PCT/US2018/012935, filed on Jan. 9, 2018, which claims priority to U.S. Provisional Application Ser. No. 62/444,079 filed on Jan. 9, 2017, the contents of each of which is are incorporated by reference in their entirety herein.

FIELD

The present disclosure generally relates to systems and methods for measuring and/or maintaining optimal growth in animals. More specifically, the present disclosure relates to systems and methods that enable a user, such as a veterinarian, zoologist, and/or pet/livestock owner, to evaluate and/or monitor body weight and other biomarkers of an animal, and/or to receive intervention recommendations for a specific at risk animal to ensure healthy and optimal growth of the animal.

BACKGROUND

In the advent of modern medicine and rapidly changing environments, evaluating and monitoring the growth phase is fundamental to the lifelong health and wellbeing of animals. A growth pattern that deviates from an optimal range or an ideal target can result from, among other factors, malnutrition, lack of exercise, external disease, or the presence of an underlying developmental disorder. Such atypical growth patterns can also predispose animals to health problems, such as obesity, undesirable comorbidities, and musculoskeletal or joint defects. Therefore, animal growth curves, especially those based on biomarkers such as weight and age, provide standards that represent the best description of physiological development from birth to adulthood and beyond.

With specific regard to humans, the World Health Organization (WHO) undertook a Multicentre Growth Reference Study (MGRS) between 1997 and 2003 to generate new growth curves for assessing the development of infants and young children around the world. These child growth charts are used to assess children's nutritional status, measure the general wellbeing of entire populations, formulate health and government policies, and plan interventions and monitor their effectiveness. The WHO MGRS child growth standards also allow trained health professionals to compare an individual child's growth and development, irrespective of geography, race, or ethnicity, to that of a healthy reference population, and promote a healthy growth trajectory.

In the same vein, recent attention has focused on optimal growth patterns and ideal body weight as they pertain to general human health and nutrition, and particularly, childhood obesity and risks of associated health problems later in life. Despite focus on ideal body weight and growth curves within the human population and childhood obesity context, analogous processes do not exist for other animals. In fact, there is limited information available on what constitutes ideal growth in non-human animals. What little information is available does not account for non-human animal gender differences, and there is even more limited information on what the ideal body weight for a particular non-human animal should be. This is further complicated by the fact that one type of animal can have numerous different and diverse breeds. For example, dog breeds can range from a 6-pound Chihuahua, to a 60-pound Golden Retriever, to a 140-pound Saint Bernard. Moreover, domestic pets or agricultural livestock are often neutered by owners, which impacts metabolism and affects growth trajectory. Many animals are also a mixture of several different breeds, meaning their physiological development or genetic predispositions cannot be classified under one distinct breed. Unlike the WHO MGRS, which provided one healthy population reference against which all developing infants and young children worldwide are measured, such a one-size-fits-all growth standard does not and cannot exist for other animals.

Thus, there remains a need for systems and methods to evaluate and monitor optimal growth in non-human animals. There also remains a need for systems and methods to determine ideal body weight for animals and provide recommendations and/or tailored interventions when such animal growth deviates from target. There further remains a need to provide growth standards—not just references—that assess the health and vitality of an animal based on ideal body weight, irrespective of breed, as well as a need for diagnosing growth abnormalities in order to maintain optimal growth in non-human animals. More specifically, what is needed in the art is an optimal animal growth application.

SUMMARY OF THE INVENTION

The present disclosure generally relates to a software application platform which provides a user with the ability to receive customized information relating to an animal's health and/or optimal growth as displayed on a graphical user interface based on data input relating to a specific animal. Specifically, a user may input data, for example, an animal specific biomarker, and subsequently receive identification relating to a specific subgroup of individual animal(s) who are at risk for growth abnormalities, and further receive information, data, and customized recommendations and/or intervention steps for the specific at risk animal relating to the animal's health, growth abnormality, or similar feature based on an analysis and determination of the biomarker as compared to a reference database. The application allows for customization of the biomarkers, information, data, and/or general inputs relating to a wide variety of animals while maintaining a display of subsequent information, data, recommendations, intervention steps, and/or other outputs relating to the monitoring and/or evaluation of the animal to allow for healthy, optimal growth.

In one embodiment, a method for diagnosing growth abnormalities in order to maintain optimal growth in non-human animals is disclosed. The method includes receiving one or more first biomarker inputs relating to a first animal, comparing the one or more first biomarker inputs of the first animal to at least one predetermined reference biomarker input stored in a reference database in order to obtain relevant health trend information relating to the first animal, and determining, based on the comparing, whether the first animal is at risk for at least one growth abnormality. The predetermined reference biomarker input includes related biomarker inputs of normal, healthy animals of the same species or within the same growth period as the first animal. The method further includes providing a subject determined to be at risk for at least one growth abnormality with a customized recommendation for lifestyle treatment options, and displaying the customized recommendation and the relevant health trend information of the first animal on a graphical user interface. A first biomarker input determined to be above or below the predetermined reference biomarker input indicates an increased likelihood in growth abnormalities in the first animal.

In another embodiment, a computer system for diagnosing growth abnormalities in order to maintain optimal growth in non-human animals is disclosed. The computer system includes a processor and a memory storing instructions that, when executed by the processor, cause the computer system to carry out the method described supra.

In yet another embodiment, a non-transitory computer-readable medium, storing instructions that, when executed by a processor, cause a computer system to diagnose growth abnormalities in order to maintain optimal growth in non-human animals is disclosed. The computer system may perform the method operations described supra.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
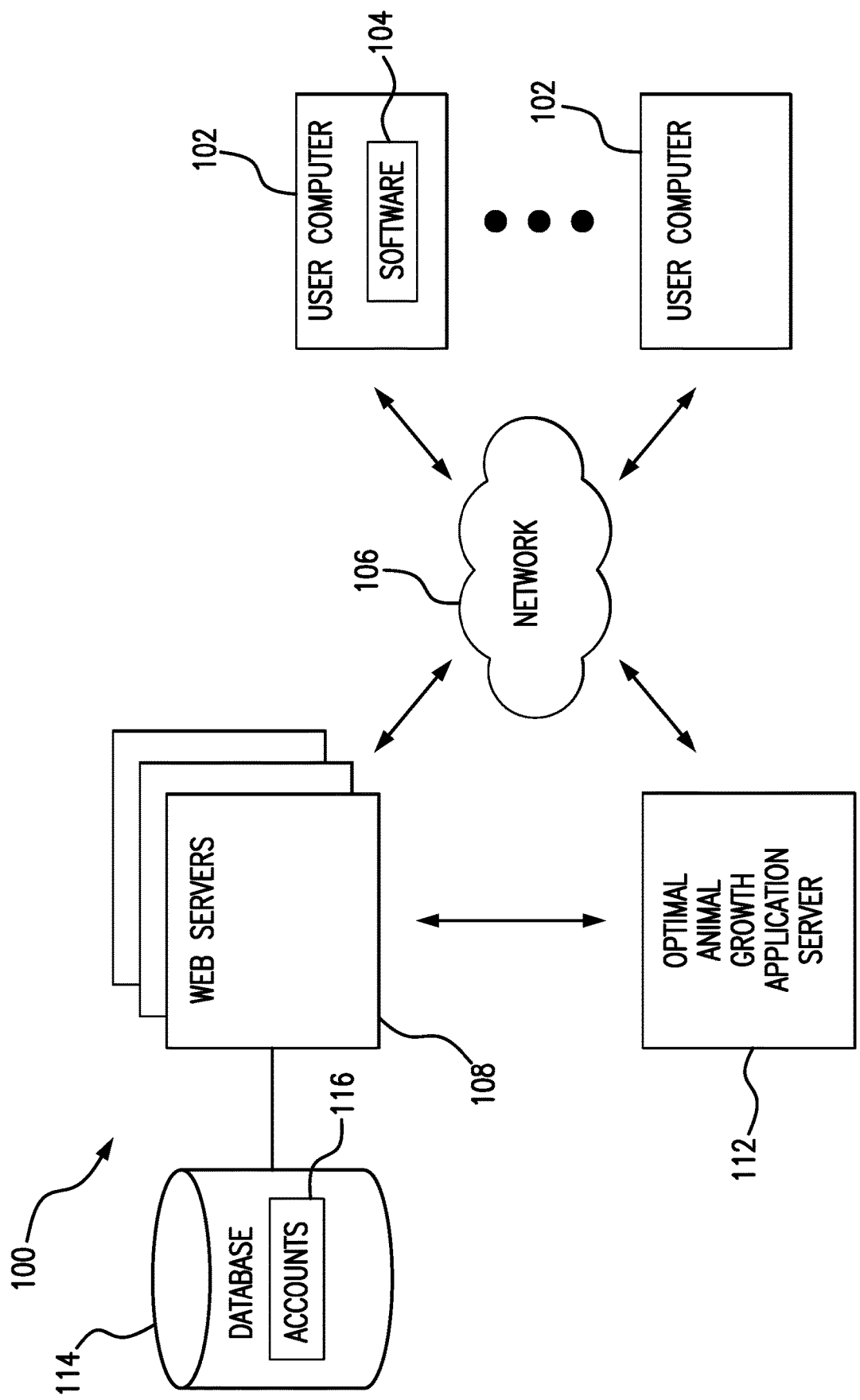
FIG. 1 illustrates a computer system configured for providing a website having an optimal animal growth application, according to one embodiment described herein.

A software application platform which provides a user with the ability to receive customized information relating to an animal's health and/or optimal growth as displayed on a graphical user interface based on data input relating to a specific animal is disclosed. Specifically, a user may input data, for example, an animal specific biomarker, and subsequently receive identification relating to a specific subgroup of individual animal(s) who are at risk for growth abnormalities, and further receive information, data, and customized recommendations and/or intervention steps for the specific at risk animal relating to the animal's health, growth abnormality, or similar feature based on an analysis and determination of the biomarker as compared to a reference database. The reference database utilizes evidenced-based growth charts for animals, derived from biomarkers such as body weight and age, among others, to create growth standards applicable to diverse breeds within a species, which account for sex and neuter status, and to recommend tailored interventions for long term health. The application allows for customization of the biomarkers, information, data, and/or general inputs relating to a wide variety of animals while maintaining a display of subsequent information, data, recommendations, intervention steps, and/or other outputs relating to the monitoring and/or evaluation of the animal to allow for healthy, optimal growth.

The terms used in this specification generally have their ordinary meanings in the art. Certain terms are discussed below, or elsewhere in the specification, to provide additional guidance in describing the systems and methods of the presently disclosed subject matter.

All percentages are by weight unless otherwise specified.

As used herein, the words "a" or "an," when used in conjunction with the term "comprising" in the claims and/or the specification, can mean "one," but they are also consistent with the meaning of "one or more," "at least one," and/or "one or more than one." Furthermore, the terms "having," "including," "containing" and "comprising" are interchangeable, and one of skill in the art will recognize that these terms are open ended terms.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

As used herein, the term "reference database" means the proprietary set of growth references, charts, data points, graphs, media, code, and information for animals of specific sex, breed, and/or size, among other measurable factors.

As used herein, the term "normal weight" or "healthy" means when an animal's weight or body mass is within about two centiles of its projected growth curve.

As used herein, the term "unhealthy" means the animal is obese, overweight, or underweight.

As used herein, the term "adult" means an animal has passed puberty and reaches its biological maturation point. Unless otherwise specified, an animal is an "adult" after about 2 years from birth.

As used herein, the term "adolescence" means the period in an animal's life between from about 6 months to about 24 months after birth, depending on the animal's adult size.

As used herein, the term "puppy" means a young dog less than about 2 years old, as measured from birth. More specifically, "puppy" means a young dog as measured from birth to about 6-18 months after birth, depending on the animal's adult size.

As used herein, the term "later in life" refers to effects measured in an animal after about the age of 2 years.

As used herein, the term "sequential" or "sequentially" means that information is input in a successive manner such that a first portion of information is input at a first time, a second portion of information is input at a second time subsequent to the first time, and so on. The time between sequential inputs can be, for example, one or several days, weeks, months, or the like.

The term "user" as used herein includes, for example, a person or entity that owns a computing device or wireless device; a person or entity that operates or utilizes a computing device or a wireless device; or a person or entity that is otherwise associated with a computing device or wireless device. It is contemplated that the term "user" is not intended to be limiting and may include various examples beyond those described.

The term "image" as used herein includes, for example, messages, photos, videos, blogs, advertisements, notifications, and various other types of media which may be visually consumed by a user. It is contemplated that the term "image" is not intended to be limiting and may include various examples beyond those described.

FIG. 1 illustrates a computing system 100 configured for providing an optimal animal growth application in which embodiments of the disclosure may be practiced. As shown, the computing system 100 may include a plurality of web servers 108, an optimal animal growth application server 112, and a plurality of user computers (for example, mobile/wireless devices) 102 (only two of which are shown for clarity), each connected to a communications network 106 (for example, the Internet). The web servers 108 may communicate with the database 114 via a local connection (for example, a Storage Area Network (SAN) or Network Attached Storage (NAS)) over the Internet (for example, a cloud based storage service). The web servers 108 are configured to either directly access data included in the database 114 or to interface with a database manager that is configured to manage data included with the database 114. An account 116 is a data object that stores data associated with a user, such as the user's email address, password, contact information, billing information, animal information, and the like.

Each user computer 102 may include conventional components of a computing device, for example, a processor, system memory, a hard disk drive, a battery, input devices such as a mouse and a keyboard, and/or output devices such as a monitor or graphical user interface, and/or a combination input/output device such as a touchscreen which not only received input but also displays output. Each web server 108 and the optimal animal growth application server 112 may include a processor and a system memory (not shown), and may be configured to manage content stored in database 114 using, for example, relational database software and/or a file system. The web servers 108 may be programmed to communicate with one another, user computers 102, and the optimal animal growth application server 112 using a network protocol such as, for example, the TCP/IP protocol. The optimal animal growth application server 112 may communicate directly with the user computers 102 through the communications network 106. The user computers 102 are programmed to execute software 104, such as web browser programs and other software application, and access web pages and/or application managed by web servers 108 by specifying a uniform resource locator (URL) that directs to web servers 108.

In the embodiments described below, users are respectively operating the user computers 102 that are connected to the web servers 108 over the communications network 106. Web pages are displayed to a user via the user computers 102. The web pages are transmitted from the web servers 108 to the user's computer 102 and processed by the web browser program stored in that user's computer 102 for display through a display device and/or a graphical user interface in communication with the user's computer 102.

In one example, information and/or images displayed on the user's computer 102 may relate to animal health information via a graph or chart accessed via an online database. The user's computer 102 may access the animal health information via the communications network 106 which, in turn, retrieves the animal health information from the web servers 108 connected to the database 114 and causes the information and/or images to be displayed through a graphical user interface of the user's computer 102. The online information and/or images, and/or the optimal animal growth application may be managed with a username and password combination, or other similar restricted access/verification required access method, which allow the user to "log in" and access the information.

It is noted that the user computer 102 may be a personal computer, laptop, mobile computing device, smart phone, tablet, video game console, home digital media player, network-connected television, set top box, and/or other computing devices having components suitable for communicating with the communications network 106. The user computer 102 may also execute other software applications configured to receive animal growth information from the optimal animal growth application, such as, but not limited to, text and/or image display software, media players, computer and video games, and/or widget platforms, among others.

Figure 2:
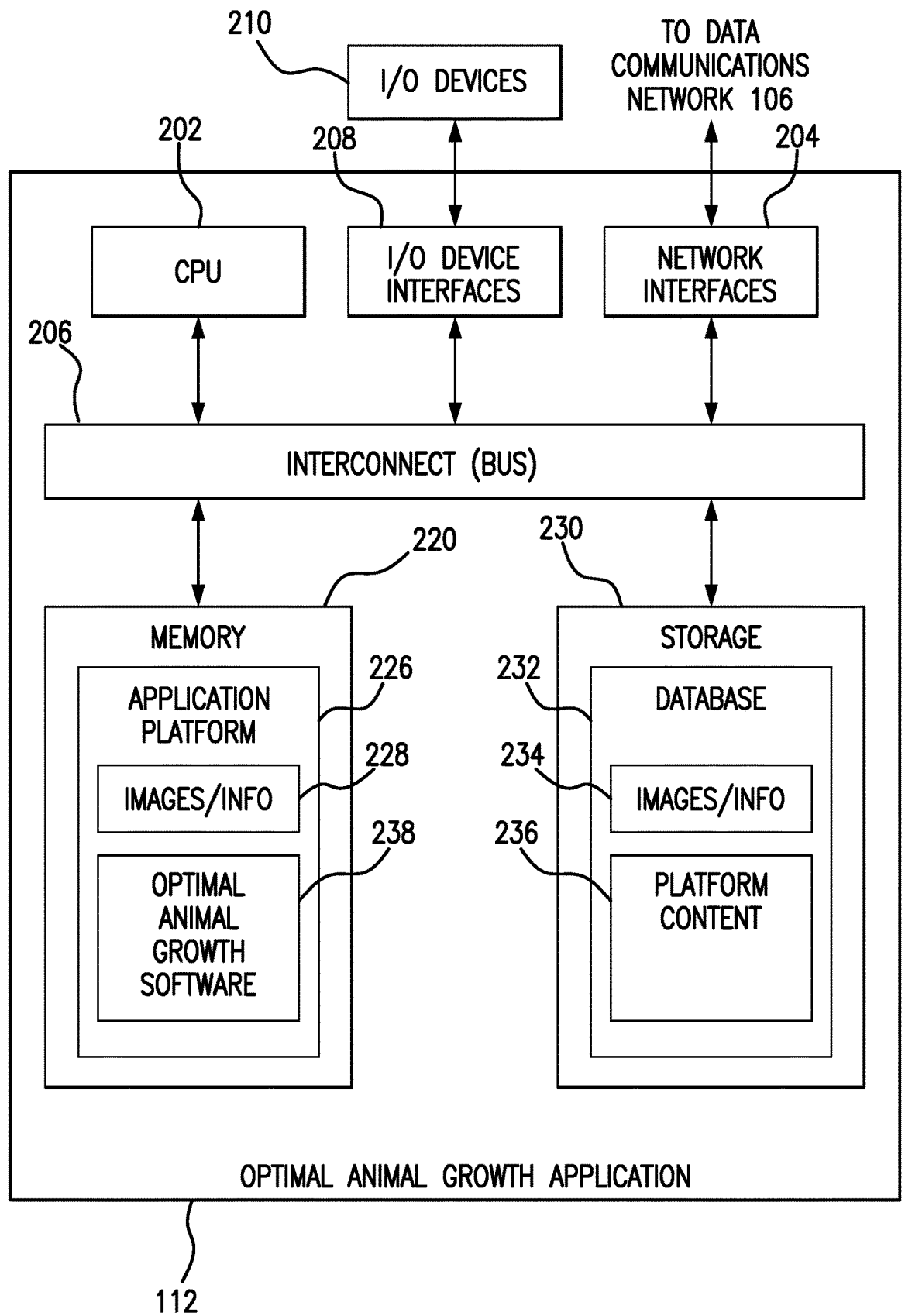
FIG. 2 illustrates a more detailed view of a server of FIG. 1, according to one embodiment described herein.

FIG. 2 illustrates a more detailed view of the optimal animal growth application server 112 of FIG. 1. The optimal animal growth application server 112 includes, without limitation, a central processing unit (CPU) 202, a network interface 204, memory 220, and storage 230 communicating via an interconnect 206. The optimal animal growth application server 112 may also include I/O device interfaces 208 connecting I/O devices 210 (for example, keyboard, video, mouse, audio, touchscreen, etc.). The optimal animal growth application server 112 may further include the network interface 204 configured to transmit data via the communications network 106.

The CPU 202 retrieves and executes programming instructions stored in the memory 220 and generally controls and coordinates operations of other system components. Similarly, the CPU 202 stores and retrieves application data residing in the memory 220. The CPU 202 is included to be representative of a single CPU, multiple CPUs, a single CPU having multiple processing cores, and the like. The interconnect 206 is used to transmit programming instructions and application data between the CPU 202, I/O device interfaces 208, storage 230, network interfaces 204, and memory 220.

The memory 220 is generally included to be representative of a random access memory and, in operation, stores software application and data for use by the CPU 202. Although shown as a single unit, the storage 230 may be a combination of fixed and/or removable storage devices, such as fixed disk drives, floppy disk drives, hard disk drives, flash memory storage drives, tape drives, removable memory cards, CD-ROM, DVD-ROM, Blu-Ray, HD-DVD, optical storage, network attached storage (NAS), cloud storage, or a storage area-network (SAN) configured to store non-volatile data.

The memory 220 may store instructions and logic for executing an application platform 226 which may include images 228 and/or optimal animal growth software 238. The storage 230 may store images and/or information 234 and other user generated media and may include a database 232 configured to store images and/or information 234 associated with the application platform content 236. The database 232 may also store application content relating to data associated with user generated media or images and other application features for providing a user with an application platform that uses evidenced-based growth charts for animals, derived from biomarkers such as body weight and age, among others, to create growth standards applicable to diverse breeds within a species, which account for sex and neuter status, and to recommend tailored interventions for long term animal health. The database 232 may be any type of storage device.

Network computers are another type of computer system that can be used in conjunction with the disclosures provided herein. Network computers do not usually include a hard disk or other mass storage, and the executable programs are loaded from a network connection into the memory 220 for execution by the CPU 202. A web TV system is also considered to be a computer system, but it may lack some of the features shown in FIG. 2, such as certain input or output devices. A typical computer system will usually include at least a processor, memory, and an interconnect coupling the memory to the processor.

Figure 3:
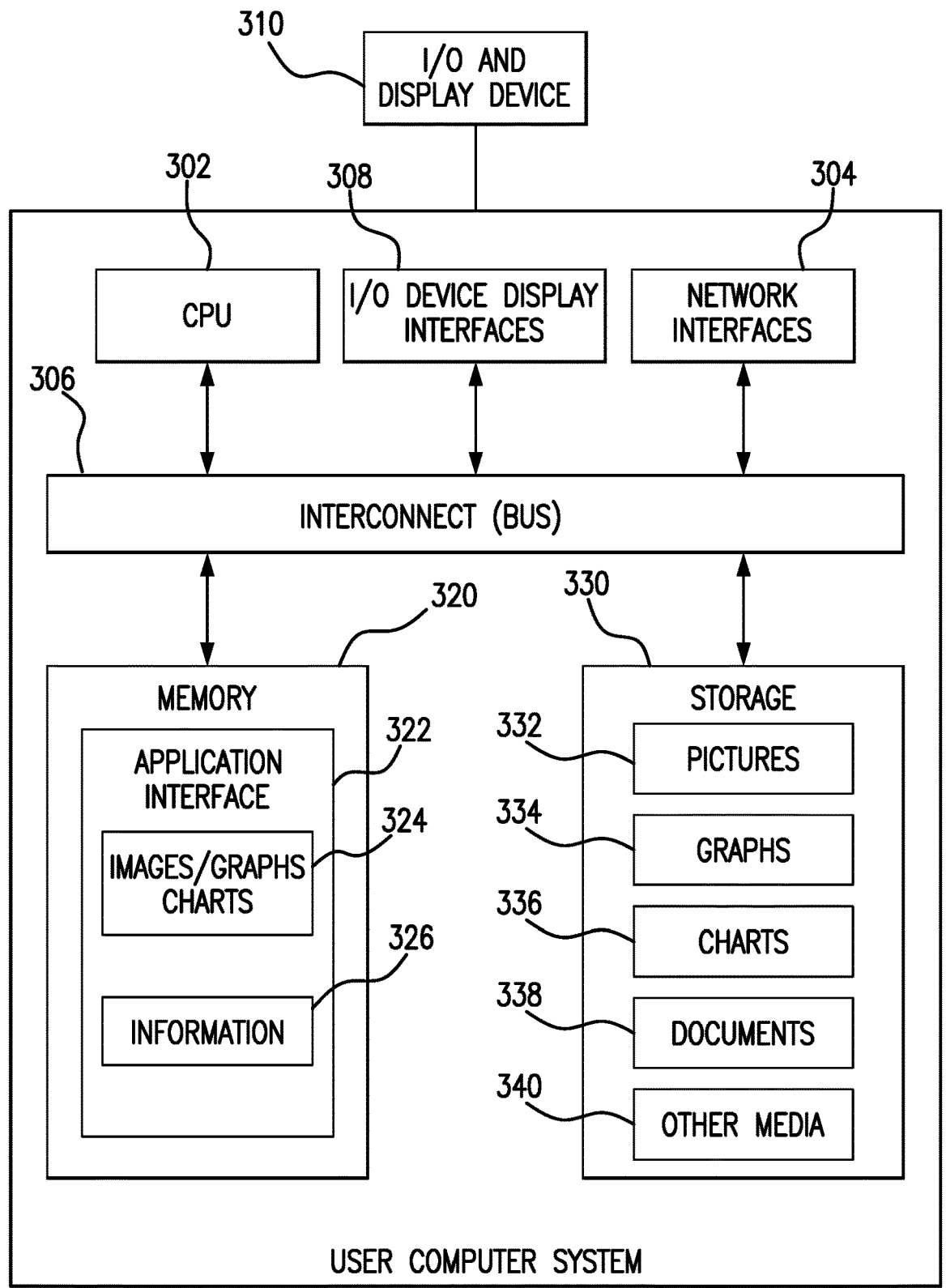
FIG. 3 illustrates a user computing system used to access a website and utilize the optimal animal growth application, according to one embodiment described herein.

FIG. 3 illustrates a user computer 102 used to access the optimal animal growth application 112 and display images and/or information associated with the application platform 226. The user computer 102 may include, without limitation, a central processing unit (CPU) 302, a network interface 304, an interconnect 306, a memory 320, and storage 330. The user computer 102 may also include an I/O device interface 308 connecting I/O devices 310 (for example, keyboard, display, touchscreen, and mouse devices) to the user computer 102.

Like CPU 202, CPU 302 is included to be representative of a single CPU, multiple CPUs, a single CPU having multiple processing cores, etc., and the memory 320 is generally included to be representative of a random access memory. The interconnect 306 may be used to transmit programming instructions application data between the CPU 302, I/O device interfaces 308, storage 330, network interface 304, and memory 320. The network interface 304 may be configured to transmit data via the communications network 106, for example, to stream or provide content from the optimal animal growth application server 112. Storage 330, such as a hard disk drive or solid-state storage drive (SSD), may store non-volatile data. The storage 330 may contain pictures 332, graphs 334, charts 336, documents 338, and other media 340. Illustratively, the memory 320 may include an application interface 322, which itself may display images 324, such as graphs or charts among others, and/or information 326. The application interface 322 may provide one or more software applications which allow the user to access media items and other content hosted by the optimal animal growth application server 112.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "analyzing" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The present example also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, read-only memories (ROMs), random access memories (RAMs), EPROMs, EEPROMs, flash memory, magnetic or optical cards, any type of disk including floppy disks, optical disks, CD-ROMs, and magnetic-optical disks, or any type of media suitable for storing electronic instructions, and each coupled to a computer system interconnect.

The algorithms and displays presented herein are not inherently related to any particular computer or other apparatus. Various general purpose systems may be used with programs in accordance with the teachings herein, or it may prove convenient to construct a more specialized apparatus to perform the required method operations. The structure for a variety of these systems will appear from the description above. In addition, the present examples are not described with reference to any particular programming language, and various examples may thus be implemented using a variety of programming languages.

As described in greater detail herein, embodiments of the disclosure provide a software application through which a user may receive customized information relating to an animal's health and/or optimal growth as displayed on a graphical user interface based on data input relating to a specific animal. Furthermore, the user may customize, via a selection of at least one biomarker, the information received, such as animal growth or health information, displayed on a graphical user interface from which the software application may apply and display relevant health information and/or an intervention recommendation.

Figure 4A:
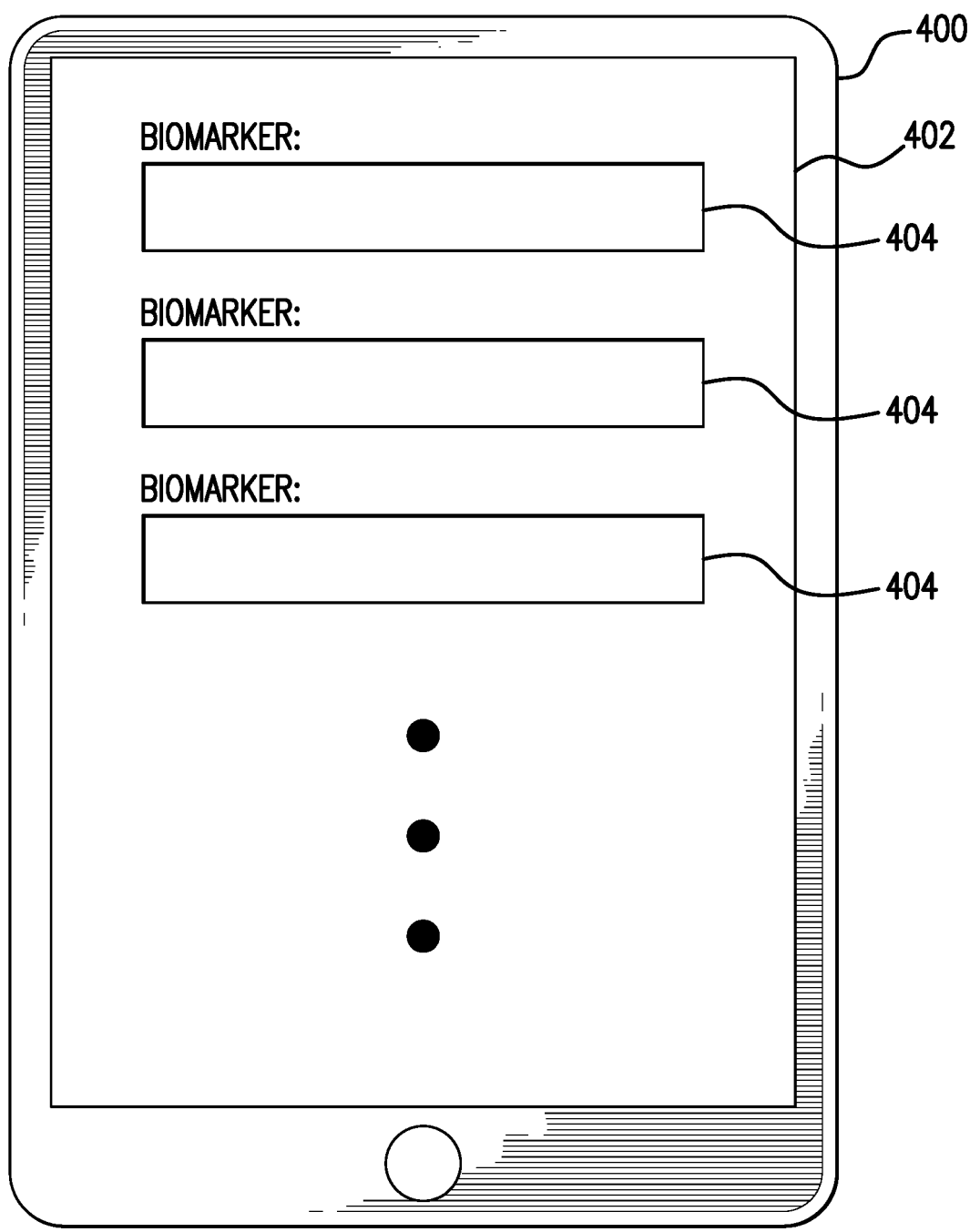
FIG. 4A illustrates a first conceptual diagram of applying an optimal animal growth application display scheme to a user interface, according to embodiments described herein.
Figure 4B:
FIG. 4B illustrates a second conceptual diagram of applying an optimal animal growth application display scheme to a user interface, according to embodiments described herein.
Figure 4C:
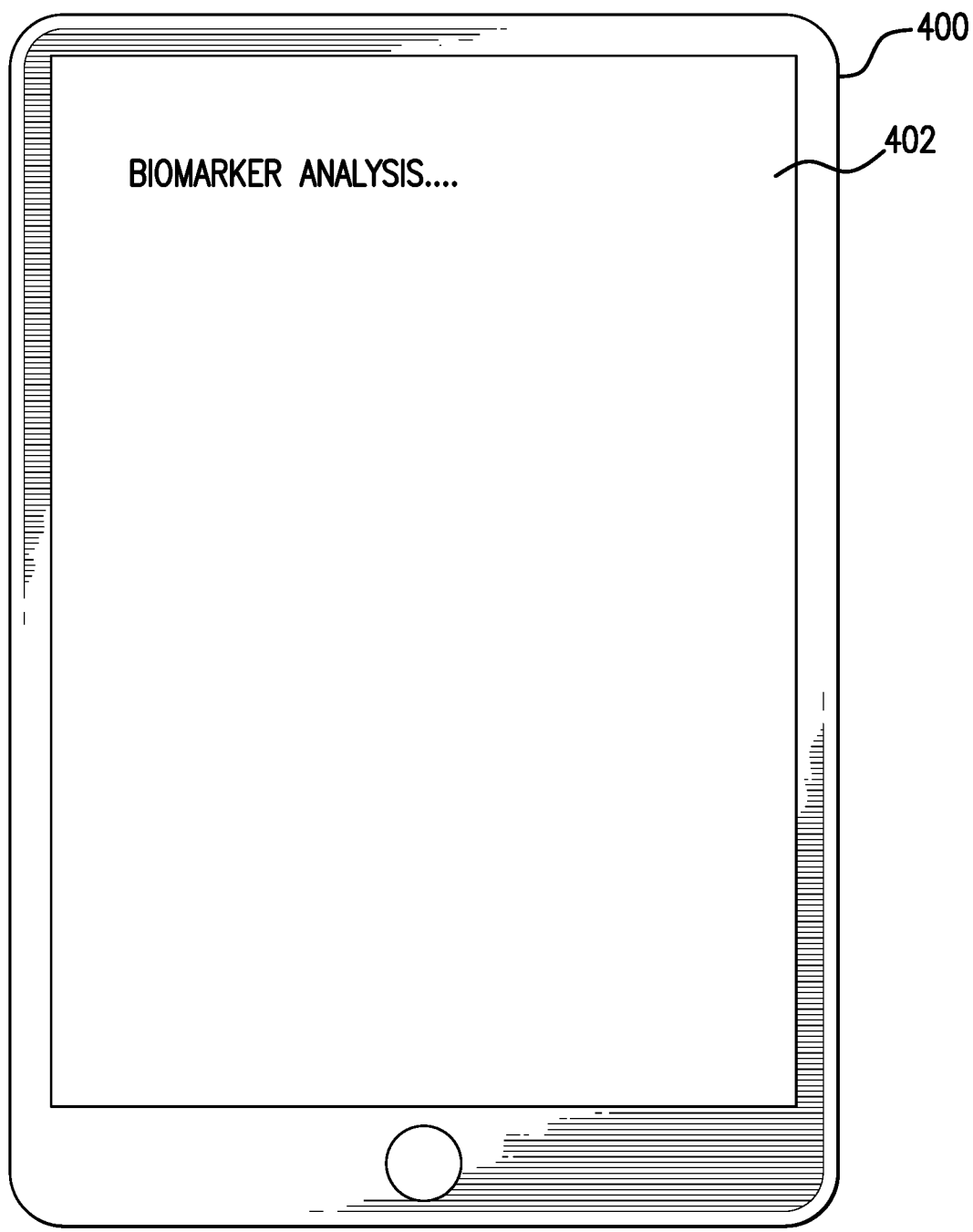
FIG. 4C illustrates a third conceptual diagram of applying an optimal animal growth application display scheme to a user interface, according to embodiments described herein.

FIGS. 4A, 4B, and 4C, respectively, are conceptual diagrams illustrating application of optimal animal growth application display schemes to a user interface 400, according to embodiments described herein. The user interfaces 400 illustrated in FIGS. 4A, 4B, and 4C are accessible, for example, via a web browser application (not illustrated) and include a plurality of web-based user interface elements, for example, a header, a footer, a body, borders, links, text blocks, graphics, images, media, charts, graphs, and the like, which are arranged to present digital information, customized recommendations, and/or images on a web page within the web browser application. For example, the user interface 400 may include a main window 402, that is configured to receive user input, and/or display information, recommendation(s), and/or images contained within the web page based on the user input.

In the embodiment illustrated in FIG. 4A and FIG. 4B, the optimal animal growth application server 112 receives a selection 404 of at least one biomarker. For example, a user may enter one or more biomarkers related to a desired animal. In certain embodiments, the one or more biomarkers may include breed and/or species of animal, approximate size, sex, date of birth, age, weight, date of measurement, neutering (if applicable), laboratory tests, consumption patterns, current diet, fluid intake, frequency of exercise, bowel movements, medical history, preexisting conditions, and/or other health related biomarker.

By way of example only, and not intended to be limiting, in one embodiment one type of biomarker input may be dog breed or dog size classification. Dog size classifications are well known in the art and based on measurements such as length of back, circumferences of neck and chest, and standing height. Dog size classifications comprise five categories: toy, small, medium, large, and giant. For example, a user can input (and the system can receive) "Jack Russell Terrier" for breed and "small" for size. If the breed of the dog or the anticipated adult size of the dog is not known, no information may be entered by user (or received by the system).

In another embodiment, neutering status may serve as a biomarker, and if performed, the date of neutering may also be provided. Neutering may affect the dog's metabolism and/or shift the dog's optimal growth curve; thus, allowing for an adjustment of reference data, if needed. In other embodiments, lab results may be entered as a biomarker input. Lab results, such as cholesterol, bone density, or genetic defects, may provide a detailed profile of the dog's health history. Furthermore, in some embodiments, exercise routine, type, and/or intensity may serve as a biomarker. For example, a dog may be walked four times a week in the afternoon for 30 minutes each; then one day per week, the dog goes to the dog park to run free for two hours. A user can rank the intensity of the exercise as low (e.g., walking), medium (e.g., dog park), or high (e.g., long distance running or sprinting). Also, in certain embodiments, frequency of bowel movements may be used as a biomarker. For example, a user can include the number of times the dog urinates and defecates on average daily. User can also detail the consistency of the feces, whether the dog has had diarrhea or if the feces are dry and retains shape. This may alert to possible gastrointestinal concerns. Other health concerns, such as preexisting conditions, may also be used as a biomarker in some embodiments. Such health concerns may include food allergies, contraction of lime disease or rabies, vaccinations, and amputations or surgeries.

In the embodiment illustrated in FIG. 4C, the optimal animal growth application server 112 analyzes the selection 404 of the at least one biomarker. A reference database is subsequently utilized to analyze the one or more biomarker input(s). In certain embodiments, the reference database may include an optimal growth standard for various animals/breeds/species, etc. The reference database may utilize evidenced-based growth charts for animals, derived from biomarkers such as body weight and age, among others, machine learning, and/or complex algorithms and code to transform the data to create growth standards applicable to diverse breeds within a species, which account for sex and neuter status.

In one embodiment, and as discussed infra, a reference database of growth charts may be generated from a retrospective observational study using body weight and age from specific animal populations collected from national primary care veterinary hospitals during routine check-ups. The database can use electronic patient medical records based on a search for the animal/breed, species, etc. and may be subject to the biomarker input. By way of example only, if a dog breed and age are entered as a biomarker, information contained with the reference database may include typical weight trends, typical body conditions, and projected weight trends and body conditions. In other embodiments, the reference database may include data of like animals with at least one body weight recorded between the ages of ten weeks and twenty-five months for modeling. Animals that receive a diagnosis of being underweight, overweight, or obese may be excluded from any modelling.

In certain embodiment, the database classifies the animal body conditions into three categories of body condition score (BCS): "thin," "normal," and "heavy." Alternatively, where BCS is measured on a five-category scale—very thin, thin, ideal weight, overweight, and markedly obese—such data can be converted to an equivalent three-category BCS.

In certain embodiments, the database may build a linear discriminant analysis models for popular animals/breeds to predict BCS in adult animals, e.g. dogs, from actual weight, gender, neuter status, and age. These models are tested on unseen validation datasets and were found to have an acceptance accuracy of about 70% to about 75% depending on breed.

In certain embodiments, the datasets are cleaned by first excluding outliers that are three times the median weight for individual dogs over one year old. All body weights are divided into 40 equal-size age groups and plotted as box-and-whisker plots. Loess regression lines, with a smoothing span of 0.8, are fitted through the upper and lower outlier limits of each bin, defined as 150% of the upper and lower whiskers. Points outside of these lines are excluded. Body-weights are converted to z-scores using an appropriate initial growth curve model, and then the distance of each point from the mean of the remaining points for that dog are calculated as a multiple of the standard deviation of those remaining points. Data points where the multiple is greater than three are excluded.

In certain embodiments of the reference database, growth centile curves are constructed using Generalized Additive Models for Location, Shape, and Scale (GAMLSS). GAMLSS is a semi-parametric modelling technique, whereby aspects of the underlying distribution are estimated as smooth functions of the predictor variables. Analyses are performed with R3.1.1 using the R package GAMLSS.

In certain embodiments, two GAMLSS models are utilized. Box-Cox Cole-Green (BCCG) models central tendency, spread, and skewness. Box-Cox Power Exponential (BCPE) additionally models kurtosis. Functions for location, scale, skewness, and kurtosis are smoothed with penalized beta splines, using the local Generalized Akaike Information Criterion to estimate the most appropriate value for the degrees of freedom. This is done using the pb( ) function in the GAMLSS R package. Smooth parameters are chosen by assessing model fit and suitability across a range of values, with a focus on those lying between the Akaike Information Criterion (AIC) and the Schwarz Bayes Criterion (SBC).

In certain embodiments, the BCPE model is fitted, initially using SBC as smoothing criterion for all parameters. Model fit is then examined. To achieve an acceptable fit, models are successively refitted adjusting the smoothing spline degrees of freedom. The modelling strategy avoids over-fitting.

In certain embodiments, the models may be displayed graphically as centile curves covering an age range from, for example, 12 weeks to 2 years, showing centiles at, for example, 0.4%, 2%, 9%, 25%, 50%, 75%, 91%, 98%, and 99.6%. Separate charts may be constructed for male and female healthy animals, and four neutering age groups, which are chosen of approximately equal size across all breeds (0 to <22 weeks, 22 to <26 weeks, 26 to <37 weeks, and >37 weeks).

Figure 4D:
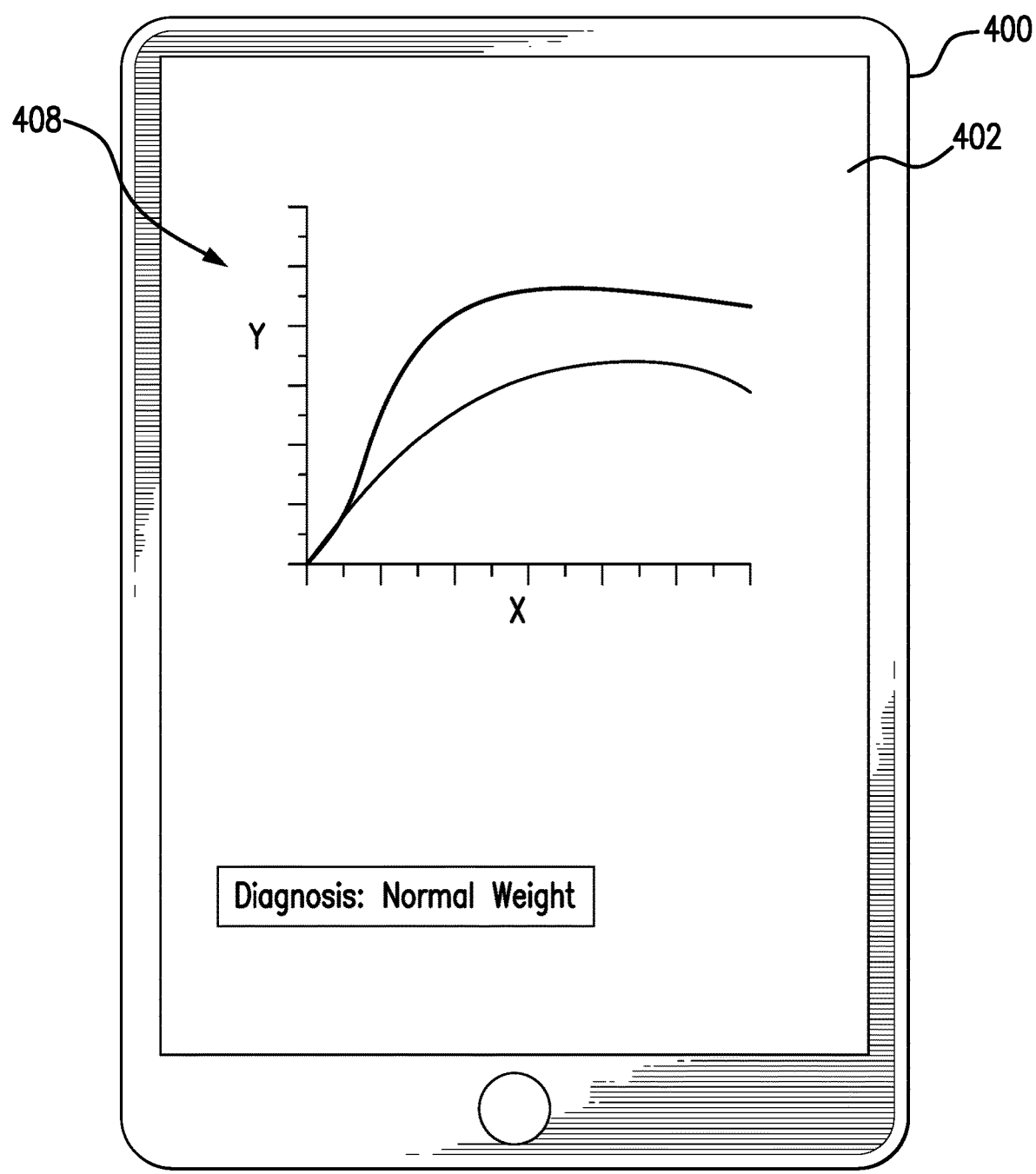
FIG. 4D illustrates a fourth conceptual diagram of applying an optimal animal growth application display scheme to a user interface, according to embodiments described herein.
Figure 4E:
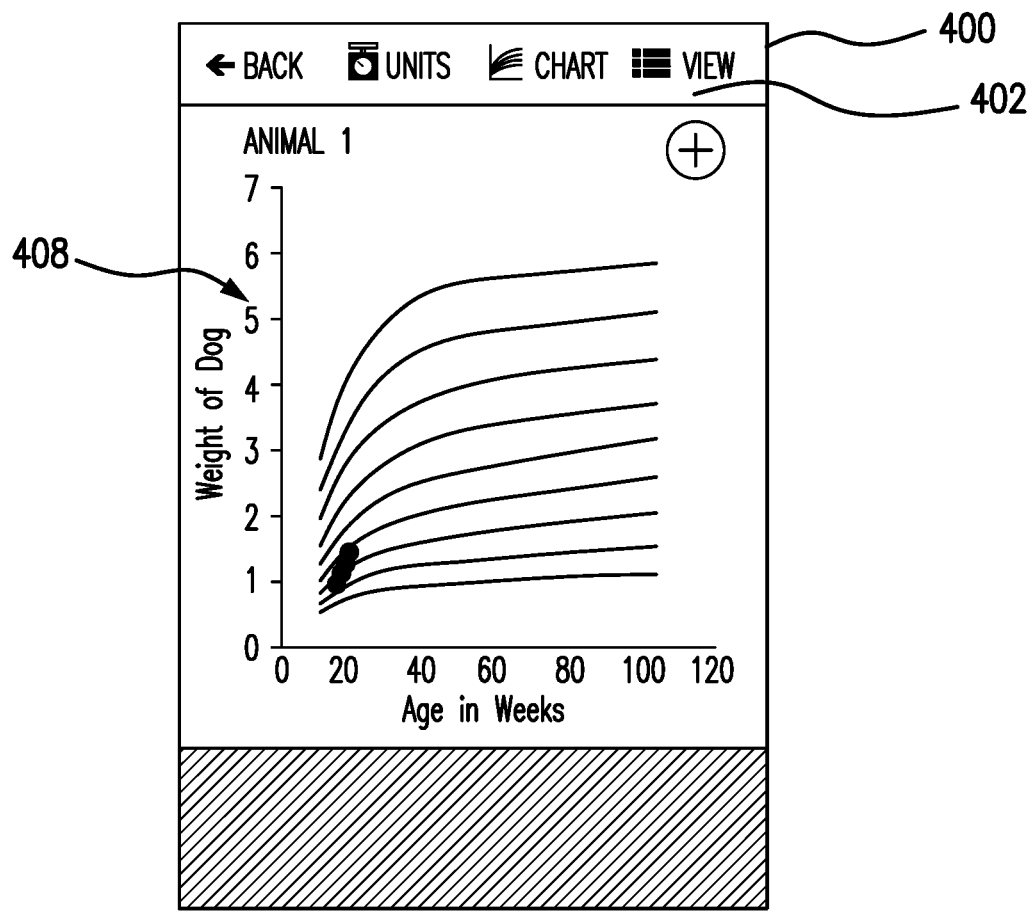
FIG. 4E illustrates a fifth conceptual diagram of applying an optimal animal growth application display scheme to a user interface, according to embodiments described herein.

In the embodiments illustrated in FIG. 4D and FIG. 4E, after analyzing the one or more biomarkers, the optimal animal growth application server 112 selects relevant health trend information of the animal based on the selection 404 of the one or more biomarker inputs and displays the relevant health trend information as an output 408 relating to the animal on the graphical user interface 400. The relevant health trend information relating to the animal may include determining characteristics and/or comparisons between the biomarker input and date in the reference database relating to similar animals. The output 408 assessment may be generated which, in some embodiments, may display the animal's overall growth within the main window 402 of the user interface 400. In certain embodiments, the output 408 assessment may include charts, graphs, graphics, messages, text, icons, or the like.

By way of example only, the output 408 of relevant health trend information may relate to dog weight. As such, the output 408 of relevant health trend information may include an indication relating to whether a dog is overweight, underweight, or normal weight—each based on the biomarkers supplied for that particular dog. As shown in FIG. 4D, the optimal animal growth application server 112 may cause the user interface 400 to display an output 408 of ideal weight versus age chart, and/or a message or recommendation relating to current dog weight.

In certain embodiments, the optimal animal growth application 112 may compare the biometric input and all previously utilized biometric inputs of the particular animal to the reference database, as shown in FIG. 4E. As such, reference curves appropriate to the given inputs are selected, each of which are unique to specific animal, and visually displayed on the user interface 400. By way of example only and as shown in FIG. 4E, a visual graph may be displayed on the user interface 400 showing the growth curve of the animal, with age on the x-axis and weight on the y-axis. On the same graph, optimal growth lines are provided at various centiles for a dog of the same sex and similar breed and size.

In another embodiment, the optimal animal growth application particularly compares the weight of an animal at about 13-15 days after birth to its birth weight. If the weight gain between the birth date and about 13-15 days after birth reflects an increase of 125% or more, then the optimal animal growth application outputs to the user that the puppy is "obese" or has an elevated risk of being overweight or obese later in adult life. Corresponding intervention recommendations are associated with such an output, as described below.

In some embodiments, an intervention may be recommended based on any one of the selection 404 of the one or more biomarkers inputs, user request, and/or the output 408 generated.

By way of example only, if the animal has a normal weight that is "within range" or "healthy" the intervention may indicate that the animal is healthy and growing optimally. In another embodiment, the intervention may recommend to continue with the current feeding and exercise regimen.

In another embodiment, where the output 408 is "obese" or indicates the animal is at risk for being overweight or obese in adult life because of its high neonatal growth rate, intervention may be recommended to the user to curb obesity before adulthood is reached. Intervention steps may suggest a change in diet or behavior to maintain or achieve healthy body weight. Diet interventions can include a switch to food that is low in fat or low in energy, but provides satiating effects. Such food can reduce stress, anxiety, and signs of begging while enhancing the animal's quality of life or activity levels. A new dietary regime is preferably implemented immediately as soon as the system determines a young animal is predisposed to obesity because it has a higher neonatal growth rate. The dietary regime can include a single diet or various types of diet, implemented daily, weekly, or monthly. Such a diet can restrict the number of calories consumed by the animal. For example, a diet can consist of an energy density less than 4,100 calories, and/or less than 15-20% fat, and/or less than 20-25% carbohydrate, and/or more than 30% protein, and/or more than 5-10% fiber. Such intervention can also include prebiotic or probiotic supplements. Behavior intervention includes increasing activity or exercise of the animal. Preferably, the dietary or behavior intervention is implemented over a period of time such that the animal's updated biomarker measurements meet the ideal weight as determined by the reference database for a specific gender and breed/size.

In an alternate embodiment, additional intervention recommendations can be made later in the adult life of the animal to prevent the animal from becoming overweight or underweight, based on the neonatal predisposition warning. For example, an owner can administer a maintenance diet for a period of time, such as three months. The owner can also administer a weight adjustment diet, which can be a weight loss diet or a weight gain diet. Such weight maintenance, weight loss, or weight gain diets are exemplified in Table 1, as they relate to a puppy/dog:

TABLE 1

| Diet | Energy Density kcal/kg | Fat % | Carbohydrate % | Protein % | Crude Fiber % | Calcium:Phosphorus |
|---|---|---|---|---|---|---|
| Puppy/Adolescence Weight Maintenance | 3800-4200 | 20-22 | 18-50 | 25-35 | 2-15 | 1:1.5 |
| Puppy/Adolescence Weight Loss | 3000-4000 | 11-20 | 25-50 | 27-38 | 4-18 | 1:1.5 |
| Puppy/Adolescence Weight Gain | 4000-4500 | 22-26 | 15-50 | 25-40 | 2-12 | 1:1.5 |
| Adult Weight Maintenance | 3400-4000 | 12-20 | 40-60 | 15-28 | 2-15 | 1:1.2 |
| Adult Weight Loss | 2500-3500 | 7-12 | 45-60 | 25-35 | 8-18 | 1:1.2 |
| Adult Weight Gain | 3800-4500 | 20-30 | 30-60 | 18-33 | 2-12 | 1:1.2 |

By way of further example, if the output 408 indicates "overweight," the intervention may recommend to reduce the amount or the number of times of feeding each day. The intervention recommendation may further suggest changing the feeding time, prescribe more exercise or higher intensity exercise, or suggest a variation in the brand or type of food, among others.

In another example, if the output 408 indicates "underweight," the intervention may recommend to increase the amount or the number of times of feeding each day, changing the feeding time, prescribe less or lower intensity exercise, suggest a variation in the brand or type of food, among others.

In yet another example, if the output 408 over several days, weeks, or months consistently indicates "overweight" or "underweight," additional intervention may be recommended, such as the need to see a veterinarian and/or perform additional behavioral or lab testing for disease.

The intervention recommendation is personalized and/or tailored based on the input of the specific animal. For example, if an underweight animal is allergic to food containing wheat, the intervention step will avoid recommending an increase of dog food containing wheat ingredients. Furthermore, if two previous veterinary visits indicated a continued increase in fat, as compared to muscle, given the animal's sex, breed and/or size, multiple intervention steps may be recommended, such as contacting and alerting the veterinarian directly at the next check-up and alerting an owner to decrease food portion size and omit treats. Alternatively, the animal's suboptimal growth can be a result of a disease, such as dwarfism or ring worm. In such instance, subsequent intervention recommendation would not repeatedly display the same initial recommendation, but may adjust or alert user to schedule a visit with a veterinarian for diagnostic testing.

By way of additional example, in certain embodiments, a dog owner may utilize an intervention recommendation related to high neonatal growth and a predisposition for obesity to evaluate the risk of obesity of puppies from a very young age. By receiving an intervention recommendation from the optimal animal growth application when the puppy is about two weeks old, the owner can apply animal maintenance techniques that first bring the puppy's growth back within the ideal and optimal range, and second, reduce the risk of future overweightness or obesity. In this way, the owner is alerted to the elevated risk pertaining to a specific dog, and both owner and the optimal animal growth application will be monitoring minor increases in the dog's body weight and/or measurable body fat content. By increasing the owner's awareness of the dog's overweight or obese development risk, preventative measures, such as reduction in caloric intake or increase in physical exercise, can be employed to eliminate effects of overweightness and obesity.

Figure 4F:
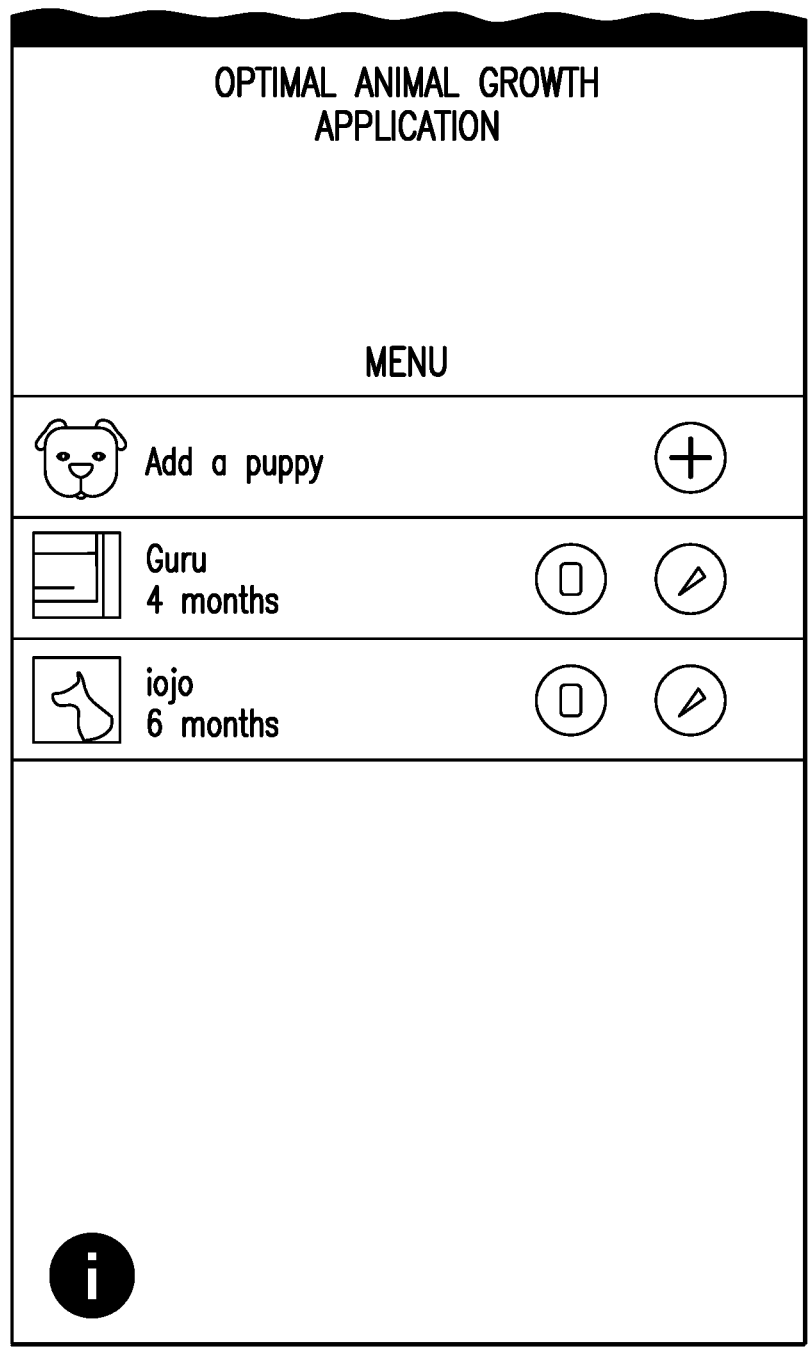
FIG. 4F illustrates a sixth conceptual diagram of applying an optimal animal growth application display scheme to a user interface, according to embodiments described herein.

In certain embodiments, the optimal animal growth application server 112 may store and/or monitor growth and/or health for multiple animals and may further be accessed and/or viewed by multiple users via multiple devices and/or displayed on multiple devices, as shown in FIG. 4F. The data of each animal and a corresponding associated profile may be transferrable to and/or accessed by different users and/or devices through the optimal animal growth application on any device or system interface. A specific animal may be identified by a unique identification tag, code, picture, number, or the like, which a user may input to retrieve the specific animal's profile and/or history.

Figure 4G:
FIG. 4G illustrates a seventh conceptual diagram of applying an optimal animal growth application display scheme to a user interface, according to embodiments described herein.

The methods and systems discussed herein may further be combined to determine multiple factors including ideal animal body weight; optimal growth (e.g., an obesity risk indicator); the effectiveness of intervention recommendations; and/or facilitate intervention by use of a device or tool containing the system. Such methods and systems can continue to be used throughout the animal's life to maintain optimal health. For example, the optimal animal growth application may be continuously updated to sequentially and periodically enter, determine, or update animal weight, age, and/or other biomarkers in order to form a medical history, as shown in FIG. 4G. From this, a life snapshot of the animal may be prepared for any given point in time. The optimal animal growth application may generate and/or update the growth curve, for example by interpolation or extrapolation. Furthermore, in some embodiments, one or more reference growth curves may be displayed, with each growth curve being associated with a centile of animals of, for example, the same species, size, sex and/or breed. The growth curve may be based at least partially on at least two weight-age values of the animal. Intervals between the different weight and age measurements after birth may be fixed (for example, every week, every two weeks, every month) or randomly (for example, one week after birth, then one month after birth, then three months after birth, then six months after birth). Continuous tracking of weight-age values may allow for the optimal growth of the animal to be evaluated. Furthermore, in some embodiments, the optimal animal growth application may display a reminder such that regular reassessments may be performed to monitor changes in the animal's development.

In another embodiment, information attained by the optimal animal growth application server 112 may be added to the reference database in order to consistently update the reference database in real-time or near real-time. As such, the real-time date may be used in clinical or veterinary studies to provide guidance about when an increase in the amount of food should be made or when to introduce different types of food, etc. As such, the use of historical data may preempt the need for future intervention by adjusting and self-updating the system.

In yet another embodiment, the optimal animal growth application server 112 may be used to monitor growth and the effectiveness of growth intervention. By tracking when an intervention recommendation is made, the timeline of how quickly (e.g., in days, weeks, months) the animal's growth curve returns to the optimal range can be monitored. Because the optimal animal growth application server 112 stores past animal data within an animal profile, intervention effectiveness may also be monitored. For example, in two instances of borderline weight gain, decreasing food intake brought the animal's growth curve back into optimal range in one month, but increase exercise by one more day per week brought the puppy's growth curve into optimal range in three weeks. As such, the optimal animal growth application server 112 may provide an alert or recommendation that in a future instance of weight gain, an increase in animal exercise may most effectively bring the animal's growth within target.

Figure 5:
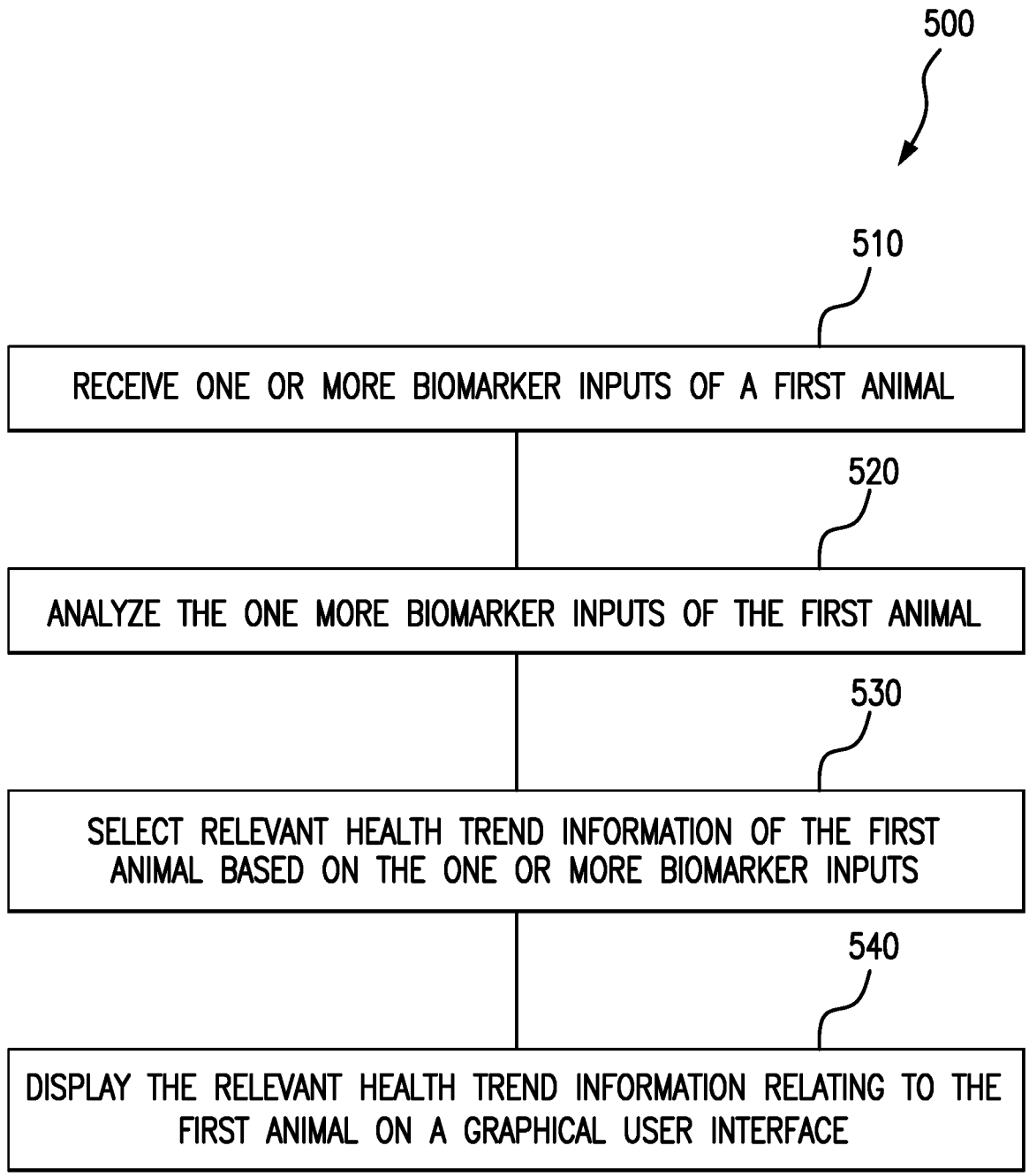
FIG. 5 schematically illustrates operations of a method for analyzing and maintaining optimal growth in non-human animals, according to one embodiment described herein.

FIG. 5 schematically illustrates operations of a method 500 for analyzing and maintaining optimal growth in animals, according to one embodiment described herein. The method generally relates to embodiments, wherein information is received and displayed on a graphical user interface. In certain embodiments, a user may input and the system receive data, for example, an animal specific biomarker, and, subsequently, the user may receive and the system display or determine information, data, recommendations, and/or intervention steps relating to the animal's health, growth, or similar feature based on an analysis and comparison of the biomarker to a reference database. The application allows for customization of the biomarkers, information, data, and/or general inputs relating to a wide variety of animals while maintaining a display of subsequent information, data, recommendations, intervention steps, and/or other outputs relating to the monitoring and/or evaluation of the animal to allow for healthy, optimal growth. At operation 510, one or more biomarker inputs of a first animal are received. In some embodiments, the first animal may be a non-human animal such as a dog or cat. The one or more biomarker inputs of the first animal may include animal identification or approximate animal size, animal breed, sex, date of birth, age, weight, date of measurement, neutering, previous laboratory test results, food and water consumption patterns, diet, exercise routine, bowel movement schedule, medical history, and/or pre-existing conditions. As discussed supra, a user may be prompted to enter the biomarker input relating to the first animal, each of which is received by the system.

At operation 520, the one or more biomarker inputs of the first animal are analyzed. In certain embodiments, the analyzing may include comparing the one or more biomarker inputs of the first animal to a reference database. The comparison obtains health trend information relating to the first animal. The reference database includes biomarker inputs related to animals of the same species as the first animal within the same growth period. The reference database stores values of given biomarkers that are ideal or optimal according to various centiles for a specific gender and breed/size of animal. For example, if the dog is female and the size is toy dog, then the reference database would have values indicating that at an age of three months, such a female toy dog should have a weight of 5 pounds if it was in the 80% centile or 5.5 pounds if it was in the 90% centile. In some embodiments, the analyzing may also include determining, based on the comparing of the one or more biomarker inputs and transforming those inputs, additional health trend information including a recommended growth weight of the first animal. By way of additional example only, if weight information of a three-month-old Great Dane dog is entered as the biomarker input, the reference database may obtain health trend information relating to standard three-month-old Great Dane dogs based on reference weight curve charts for the animal classification and/or breed.

In some embodiments, the comparison may also calculate the difference between the biomarker input versus a like value from the reference database. For example, in the case where a dog weighs 10 pounds, but the reference database indicates for that gender and breed/size of dog, at that specific age, the dog should weigh 8 pounds, the analyzing would calculate a difference of 10−8=+2, and further calculate the percent by which the dog is suboptimal. By way of continued example, the dog's percent is +25% (+2÷8=0.25).

At operation 530, relevant health trend information of the first animal is selected based on the one or more biomarker input. The health trend information may include a growth curve, ideal body weight chart or graph, and/or recommended intervention steps relating to the first animal.

At operation 540, the relevant health trend information relating to the first animal is displayed on a graphical user interface. For example, the calculated comparison value, discussed supra, may be displayed on the graphical user interface along with an alert or recommendation. An alert or recommendation may be displayed depending on the value calculated in the comparison. For example, if the calculated difference between the biomarker weight input and the reference database weight, discussed supra, provided a percent of ±5%, then an alert or recommendation stating "healthy" or "within range" may be displayed on the graphical user interface. However, if the calculated different between the biomarker weight input and the reference database weight provided a percent difference of +20%, then an alert or recommendation stating "overweight," status may be displayed on the graphical user interface.

In certain embodiments, if the alert or recommendation provides a "healthy" status, such alert or recommendation may be directly sent to display on the graphical user interface. However, if the alert or recommendation provides an unhealthy status (e.g., "underweight," "overweight," or "obese"), then the alert or recommendation may further provide an intervention recommendation to be displayed on the graphical user interface.

The intervention recommendation may provide one or a plurality of recommended intervention steps. For example, if the animal is "overweight," intervention recommendations may include "exercise pet more" or "adjust and decrease food intake." Conversely, if the dog is "underweight," intervention recommendations may include "supplement dry dog food with high protein wet dog food once per day" or "monitor and schedule visit with veterinarian."

In some embodiments, the method 500 may also include determining a body condition of the first animal based on the one or more biomarker inputs, and displaying the body condition of the first animal on the graphical user interface.

Furthermore, in some embodiments, the method 500 may further include determining a projected growth potential of the first animal based on a comparison of the one or more biomarker inputs and information from the reference database relating to the species or breed of the first animal, and displaying the projected growth potential of the first animal on the graphical user interface.

In other embodiments, the method 500 may also include calculating, based on the one or more biomarker inputs of the first animal, the difference between the weight of the first animal and the recommended growth weight of an ideal animal of the same species in a similar growth stage, determining if the difference is within two centiles of the recommended growth weight, and displaying a recommendation on the graphical user interface based on the determination. In some embodiments, the recommendation may be an intervention step if the difference is not within two centiles of the recommended growth weight.

Figure 6:
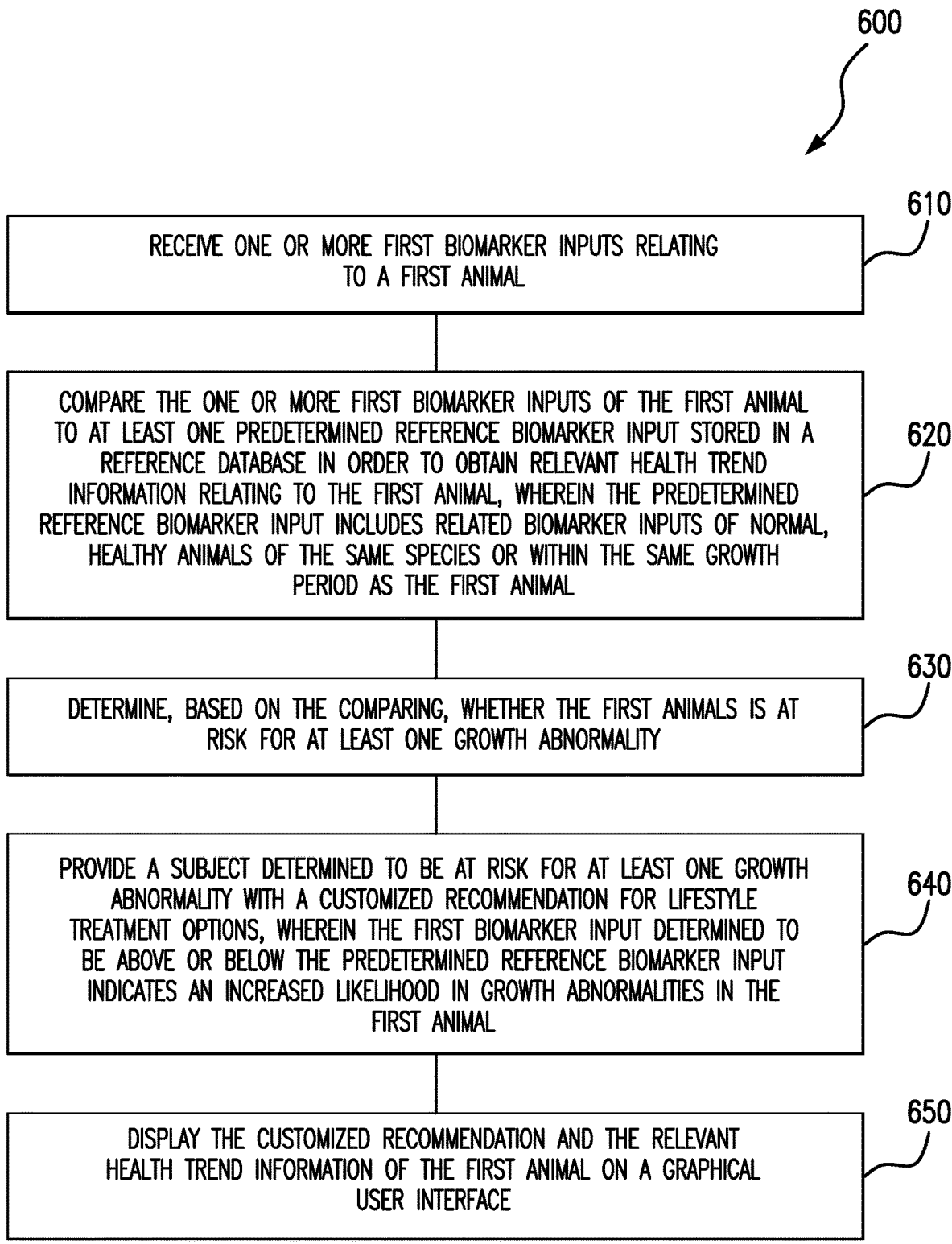
FIG. 6 schematically illustrates operations of a method of diagnosing growth abnormalities in order to maintain optimal growth in non-human animals, according to one embodiment described herein.

FIG. 6 schematically illustrates operations of a method 600 for diagnosing growth abnormalities in order to maintain optimal growth in an animal, according to one embodiment described herein. The method specifically relates to receiving of specific biomarker information and subsequently identifying a specific subgroup of individual animal(s) who are at risk for growth abnormalities, and further receiving information, data, and customized recommendations and/or intervention steps for the specific at risk animal relating to the animal's health, growth abnormality, or similar feature based on an analysis and determination of the biomarker as compared to a reference database. At operation 610 one or more first biomarker inputs relating to a first animal are received. In some embodiments, the first animal may be a non-human animal such as a dog or cat. The one or more biomarker inputs of the first animal may include animal identification or approximate animal size, animal breed, sex, date of birth, age, weight, date of measurement, neutering, previous laboratory test results, food and water consumption patterns, diet, exercise routine, bowel movement schedule, medical history, and/or pre-existing conditions. As discussed supra, a user may be prompted to enter the biomarker input relating to the first animal.

At operation 620, the one or more first biomarker inputs of the first animal are compared to at least one predetermined reference biomarker input stored in a reference database. The comparing can obtain relevant health trend information relating to the first animal. The predetermined reference biomarker input includes related biomarker inputs of normal, healthy animals of the same species or within the same growth period as the first animal.

The comparison can obtain health trend information relating to the first animal. The reference database includes biomarker inputs related to animals of the same species as the first animal within the same growth period. The reference database stores values of given biomarkers that are ideal or optimal according to various centiles for a specific gender and breed/size of animal.

At operation 630, a determination is made, based on the comparing, as to whether the first animal is at risk for at least one growth abnormality. In some embodiments, the determining includes calculating a recommended growth weight of the first animal. In certain embodiments, an at risk first animal may be diagnosed with the at least one growth abnormality, among other suitable diagnoses.

At operation 640, a subject determined to be at risk for at least one growth abnormality is provided with a customized recommendation for lifestyle treatment options. The first animal may maintain an increased likelihood of growth abnormalities if the first biomarker input is determined to be above or below the predetermined reference biomarker input.

At operation 650, the customized recommendation and the relevant health trend information of the first animal is displayed on a graphical user interface. The customized recommendation is an intervention step for correction of the growth abnormality. As such, the customized recommendation may provide one or a plurality of recommended intervention steps for the specific, identified at risk animal(s). For example, if the animal is "overweight," intervention recommendations may include "exercise pet more" or "adjust and decrease food intake." Conversely, if the dog is "underweight," intervention recommendations may include "supplement dry dog food with high protein wet dog food once per day" or "monitor and schedule visit with veterinarian." Furthermore, the relevant health trend information includes a growth curve and ideal body weight chart.

In some embodiments, the method 600 may further include calculating, based on the one or more first biomarker inputs of the first animal, the difference between the weight of the first animal and a recommended growth weight of an ideal animal of the same species in a similar growth stage as the first animal, determining if the difference is within about two centiles of the recommended growth weight, and displaying a recommendation on the graphical user interface based on the determination, wherein the recommendation includes a tailored intervention step if the difference is not within about two centiles of the recommended growth weight. The tailored intervention step can be a customized recommendation for correction of the weight abnormality.

In other embodiments, the method 600 can further include determining a projected growth potential of the first animal based on a comparison of the one or more first biomarker inputs and information stored in the reference database relating to the species or breed of the first animal, and displaying the projected growth potential of the first animal on the graphical user interface.

EXAMPLES

The present disclosure will be better understood by reference to the following Example(s), which are provided as exemplary of the present disclosure and not by way of limitation.

Example 1: Using the Optimal Animal Growth Application by a Breeder

The user is a dog breeder specializing in breeding purebred dogs. The dog breeder has access to puppies from the moment of birth. In this example, the dog breed is a Cavalier King Charles Spaniel, and the litter has four puppies, designated Puppy A (female), Puppy B (male), Puppy C (male), and Puppy D (male).

Puppies are weighed immediately after birth. The breeder inputs the date of birth, birth weight, gender, and size measurements (such as length, height, and head circumference) of each puppy into the appropriate animal profile of the optimal animal growth application. The breeder also notes additional physical attributes, such as color and texture of fur. Each puppy has its own profile within the program. Breeder can customize each puppy's profile by entering a name, such as "Puppy A," "Spring Batch #1," or "Alfie." Each profile can also be associated with the breeder, such as by the breeder's username, email, or phone number. The computer and/or program can store each puppy profile locally or on a storage server or network.

The breeder subsequently weighs the puppies each week and measures other biomarkers, such as fluid intake or food consumption amounts and habits. The breeder may also note the type of dog food used. The breeder enters this information into the program, and uses the growth curves generated from weekly inputs to monitor each puppy's individual development. The breeder compares the output graphics of each puppy's statistics with its siblings, and can also compare to previous generations of litters from the same birth mother or a different birth mother of the same dog breed, as stored by the optimal animal growth application.

In particular, the breeder weights and measures puppy biomarkers around days 13, 14, and 15 from birth. The optimal animal growth application determines and calculates the weight gain of each puppy between birth and about days 13-15 of age. If the weight gain is 125% or more, the program indicates a warning that the puppy is predisposed to being overweight in adulthood.

More generally, based on inputs from the first eight weeks since the birth of the litter, the optimal animal growth application provides an indication to breeder that Puppy A is projected to grow according to the 40% centile of female Cavalier King Charles Spaniels, Puppy B to the 80% centile of male Cavalier King Charles Spaniels, and Puppies C and D are both to the 65% centile of male Cavalier King Charles Spaniels.

Over the course of the twelfth, thirteenth, and fourteenth weeks, the breeder notices Puppy C's actual growth curve is diverging and lower than Puppy D's growth curve, crossing one centile and nearing a deviation of two centiles. However, Puppy D's food consumption, fluid intake, level of exercise, physical appearance, and observable behavior is the same as Puppies A, B, and D. The optimal animal growth application may initiate a warning of Puppy C being possibly "underweight." When Puppy C's growth curve crosses two centiles at the fifteenth week, the optimal animal growth application may output an "underweight" warning to the breeder. In addition, the optimal animal growth application suggests increasing food amount, adjusting for the type of food, and/or alerting a veterinarian.

At the sixteenth week, breeder takes all four puppies for their 4-month check-up. The breeder reports the observed growth of each puppy and discusses Puppy C's growth deviation from Puppy D. The veterinarian performs initial blood work and diagnostic health assessment. Puppy C's lab results all indicate the animal is healthy. The veterinarian advises the breeder to continue monitoring Puppy C's status, but maintain the same food, fluid, and exercise routine as Puppies A, B, and D.

Over the next two weeks, Puppy C's growth curve stops decreasing from that of Puppy D's, and begins to track the 60% centile line for male Cavalier King Charles Spaniels. The optimal animal growth application adjusts and indicates to breeder that Puppy C is now anticipated to grow optimally at about the 60% centile reference curve.

The breeder continues to input weekly data for each puppy, and each puppy's history is charted and saved with its respective profile in the optimal animal growth application. At six months from birth, the breeder is ready to sell the puppies to pet owners and other buyers.

Example 2: Using the Optimal Animal Growth Application by a Pet Owner

The user is a pet owner who purchases a Cavalier King Charles Spaniel puppy from the breeder in Example 1 above when the puppy is about six months old. The pet owner buys Puppy A. Rather than start a new dog profile, the data recorded by the breeder in the optimal animal growth application can be accessed or transferred to the pet owner. The pet owner may update the user information on the optimal animal growth application. The pet owner may also access Puppy A's history online over the Internet by logging into the optimal animal growth application server, and providing the breeder's contact information or Puppy A's profile identification.

The pet owner takes measurements of Puppy A every two weeks and notes the food and fluid intake, amount of exercise, and brand/type of dog food used. Biomarkers such as age and weight on a particular day are also input into the optimal animal growth application. The optimal animal growth application tracks and graphs Puppy A's development beginning from the date the pet owner bought it from the breeder, but the entire animal history is available to the pet owner.

At about eight months, the pet owner starts to notice that Puppy A is gaining weight and the appearance of the coat/fur is less shiny. The pet owner preemptively sees a veterinarian, before Puppy A's growth curve has crossed two centiles. At the veterinarian's office, the pet owner and veterinarian review Puppy A's growth curve and identify that the weight gain started after the pet owner switched to a different brand/type of dog food. The veterinarian may suggest that the pet owner switch back to the previous brand/type of dog food, or supplement the current brand of dog food with wet food. The pet owner adjusts Puppy A's diet accordingly, and in a few weeks, Puppy A's growth curve has stopped increasing. The owner also adds one extra walk per week to Puppy A's routine. Puppy A's development remains close to its ideal weight curve until it reaches adulthood at two years of age.

Example 3: Using the Optimal Animal Growth Application by Veterinarian

Example 3 demonstrates how the presently disclosed subject matter can assist a veterinarian as a tool to increase and promote regular visits with pets and pet owners. At the initial puppy visit, the veterinarian collects the pet name, date of birth, sex, breed, and pet owner information, such as address, contact numbers, and method(s) of payment. The veterinarian creates the puppy's profile and enters the initial input into the optimal animal growth application. In addition, the veterinarian provides the pet owner with paper charts, pamphlets, booklets, or other resources related to the optimal animal growth application and how monitor and evaluating the puppy's development and growth. The paper charts also include a specific password that allows the pet owner to download and/or access the optimal animal growth application through the Internet or a mobile application to view the specific puppy's information. The owner has the ability to enter additional input in the interim between veterinary visits. A password may be unique to a specific dog, such that the veterinarian has user and administrator rights to the profiles of all his or her pet patients. The pet owner can only view and add to his or her pet's profile, but not the profiles of the veterinarian's other patients.

Once the puppy profile is set up and data logging begins, the pet owner periodically updates the puppy profile with new biomarker measurements. Simultaneously, the veterinarian can view the recent inputs, see outputs and suggested interventions by the optimal animal growth application, and monitor the puppy's actual growth curve. Based on the inputs and the optimal animal growth application's recommended interventions, the veterinarian can further provide real-time, human, and personalized intervention steps to compliment, supplement, or override the optimal animal growth application's intervention steps. The veterinarian and pet owner can also mutually decide to turn off the optimal animal growth application's intervention recommendations, and only allow a vet to pursue an intervention if the puppy's growth curve increases or decreases by two centiles.

With the consent of the pet owner and veterinarian, the data entered into the optimal animal growth application for individual puppies can be further collected and tabulated by the optimal animal growth application to help improve correlation of reference growth curves in the reference database. Periodic updates to the program or application executing the optimal animal growth application for monitoring optimal growth includes such recent real-time data to provide better and more accurate growth standards for veterinarians and pet owners.

Example 4: Using the Optimal Animal Growth Application for Ongoing Measurement

The systems and methods for monitoring, evaluating, and maintaining optimal growth are especially useful for the development of a puppy into adulthood. Likewise, ongoing measurements are useful in allowing a pet owner or veterinarian to monitor adult ideal weight. In Example 4, the pet owner acquires a puppy when the puppy is at an age of four months. No prior biomarker data is available, so the pet owner establishes the puppy's initial profile on the optimal animal growth application via a user device. Since no previous data was available, the pet owner is particularly careful to take daily biomarker measurements of the puppy.

After the first month, the pet owner scales back the biomarker measurements to once per week. At the six-month mark, the pet owner takes the puppy to the veterinarian to get neutered. This information is input into the puppy's profile, noting the date and medical procedure. After the neutering, the puppy's weight slowly increases and its actual growth curve starts to deviate from the ideal growth reference curve. The optimal animal growth application generates an initial output warning indicating the puppy can become overweight. Likewise, since the neutering procedure was inputted, the optimal animal growth application notifies the pet owner that the puppy's metabolism is slowed, and suggests the owner decrease the food amount slightly and/or increase exercise to the puppy. The pet owner makes the appropriate reduction in food intake by the puppy, and logs data every few days. The optimal animal growth application adjusts to the puppy's actual growth curve, post-neutering, and determines which centile is ideal for the neutered puppy's growth. The pet owner continues to monitor the dog's growth up through two years.

Once the dog has achieved optimal growth from puppy to adult stage, the optimal animal growth application may continue to be used to monitor an adult dog's ideal weight. Here, the centile of the dog when it reaches adulthood is initially set as the ideal weight. The pet owner continues to input the adult dog's weight, food and fluid intake, medical episodes or anomalies, and other data weekly or monthly into the optimal animal growth application. The growth curve of the adult dog should be a flat plateau of its ideal weight since the dog is no longer growing. However, if subsequent data points of the dog, as compared to the ideal weight shows a difference of more than 5% by weight from the ideal weight, the optimal animal growth application will generate an output notifying the owner that the adult dog is "overweight" or "underweight," or worse, "obese." The optimal animal growth application then recommends intervention to bring the adult dog's weight back to the ideal, such as altering the type of food, when to feed the dog, and the amount of exercise the dog receives.

The pet owner continues to input ongoing measurements of the adult dog into the optimal animal growth application. Later life events, such as surgery or medical ailments, are also inputted with the appropriate date such that the optimal animal growth application can adjust and adapt intervention steps to the adult dog. For example, if the dog develops a food allergy at an age of 4 years, intervention steps after that time will avoid suggesting dog food brands with ingredients that exacerbate the dog's food allergy.

Example 5: Using the Optimal Animal Growth Application for Customized Intervention In this instance, the subject animal is a purebred German Shepherd. The first input of the dog's biomarkers is taken at two weeks of age, in the morning before feeding. Weight is measured biweekly on the same day at the same time. However, the pet owner logs other biomarkers daily, such as the amount of food eaten, the type of food (dry or wet), water intake, any outside sources of food such as treats, exercise, and bowel movements. A veterinarian attends to the dog every six months.

The user inputs all information into a device containing the optimal animal growth application. Every two weeks, when the user inputs a new biweekly weight data point, the optimal animal growth application generates and/or updates a continuing curve, which maps the dog's actual growth since birth. The optimal animal growth application compares the dog's individual progress to that of the size category for German Shepherd dogs. The graphical user interface of the device displays a graph showing the dog's individual weight and growth curve and the centiles for optimal growth of that dog size.

At the six-month check-up and the one-year check-up, the veterinarian collects blood samples, performs routine disease checks, and tests for vitamin deficiencies. The veterinarian inputs these lab results into the appropriate profile of the optimal animal growth application.

For one month preceding the dog's 18-month check-up, the user notices that the dog's growth curve crosses two centiles in the upward direction. The system indicates the dog is "overweight." The system initiates an intervention recommendation, and thus notifies the owner of possible adverse weight gain, with an initial recommendation to increase exercise and decrease food intake. At the 18-month check-up, the latest lab results are input into the system.

Given the new input, the optimal animal growth application may recommend an updated and/or additional intervention: switch dog food brand or decrease food intake, but do not exercise dog due to possible hip dysplasia, which is prevalent in the German Shepherd breed. The veterinarian receives this information, and executes additional tests, such as a bone density test and an X-ray of the dog to determine the prevalence of hip dysplasia. The additional intervention steps indicate the dog is suffering from hip dysplasia. The diagnosis of this disease is input into the optimal animal growth application. Accordingly, the user switches the type of dog food. The optimal animal growth application continues to monitor the dog after food intake and amount adjustments. The optimal animal growth application provides and analyzes that the dog's growth curve is moving toward the original optimal growth range. The dog continues to be fed the new type of dog food, and schedules regular veterinarian appointments to check the status of the hip dysplasia.

Benefits of the present disclosure include the ability to preliminarily measure and examine growth and health conditions of an animal without attaching sensors to the animal body or conducting additional invasive procedures. Other benefits include an efficacious system that uses personalized and anticipatory guidance, which may start at the birth of the animal. Such a system is not constrained to purebred animals, and is applicable to any type or age of animal. Further benefits include the avoidance of face-to-face intervention with an animal health specialist. A user may send data and media including text, photos, charts, graphs, animal profiles, etc. to another user (i.e., a veterinarian) via a messaging system and/or the Internet in real-time or near real-time in order to address an animal concern or an intervention recommendation. As such, a cost savings and time reduction is realized relating to such animal concerns.

Additional benefits of the present disclosure include diagnosing of an animal as at risk for growth abnormalities, including but not limited to excessive or insufficient weight, excessive or insufficient height, illness, deficiencies, and/or disease. By doing so, the disclosure allows for the identification of a specific subgroup of individuals (e.g., those at risk growth abnormalities), and also allows for an intervention to be chosen for specific animals at risk. An at risk animal can subsequently be provided with diet and/or lifestyle treatment options to reduce the effects of the risk, cure or reduce the effects of the disease, and/or to improve quality of life, among other benefits.

While the foregoing is directed to embodiments described herein, other and further embodiments may be devised without departing from the basic scope thereof. For example, aspects of the present disclosure may be implemented in hardware or software or in a combination of hardware and software. One embodiment described herein may be implemented as a program product for use within a computer system. The program(s) of the program product define functions of the embodiments (including methods described herein) and can be contained on a variety of computer-readable storage media. Illustrative computer-readable storage media include, but are not limited to: (i) non-writable storage media (for example, read-only memory devices within a computer such as CD-ROM disks readable by a CD-ROM drive, flash memory, ROM chips or any type of solid-state non-volatile semiconductor memory) on which information is permanently stored; and (ii) writable storage media (for example, floppy disks within a diskette drive or hard-disk drive or any type of solid-state random-access semiconductor memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto that are apparent to those skilled in the art upon reading of the specification and a study of the drawings are included within the true spirit and scope of the present disclosure. Is it therefore intended that the following appended claims include all such modifications, permutations, and equivalents as fall within the true spirit and scope of these teachings. Although one or more embodiments have been described herein in some detail for clarity of understanding, it should be recognized that certain changes and modifications can be made without departing from the spirit of the disclosure. The embodiments described herein can employ various computer-implemented operations involving data stored in computer systems. Furthermore, the embodiments described herein employ various computer-implemented operations which can be adapted to be part of a computer system, the cloud, etc. For example, these operations can require physical manipulation of physical quantities—usually, though not necessarily, these quantities can take the form of electrical or magnetic signals, where they or representations of them are capable of being stored, transferred, combined, compared, or otherwise manipulated. Further, such manipulations are often referred to in terms, such as producing, yielding, identifying, determining, comparing, receiving, storing, calculating, or generating. Any operations described herein that form part of one or more embodiments of the disclosure can be useful machine operations. In addition, one or more embodiments of the disclosure also relate to a device or an apparatus for performing these operations. The apparatus can be specially constructed for specific required purposes, or it can be a general purpose computer selectively activated or configured by a computer program stored in the computer. In particular, various general purpose machines can be used with computer programs written in accordance with the teachings herein, or it can be more convenient to construct a more specialized apparatus to perform the required operations.

The embodiments described herein can be practiced with other computer system configurations including hand-held devices, microprocessor systems, microprocessor-based or programmable consumer electronics, minicomputers, mainframe computers, and the like.

One or more embodiments of the present disclosure can be implemented as one or more computer programs or as one or more computer program modules embodied in one or more computer readable media. The term computer readable medium refers to any data storage device that can store data which can thereafter be input to a computer system—computer readable media can be based on any existing or subsequently developed technology for embodying computer programs in a manner that enables them to be read by a computer. Examples of a computer readable medium include a hard drive, network attached storage (NAS), read-only memory, random-access memory (e.g., a flash memory device), a CD (Compact Disc), a CD-ROM, a CD-R, or a CD-RW, a DVD (Digital Versatile Disc), a magnetic tape, and other optical and non-optical data storage devices. The computer readable medium can also be distributed over a network coupled computer system so that the computer readable code is stored and executed in a distributed fashion.

Although one or more embodiments of the present disclosure have been described in some detail for clarity of understanding, it will be apparent that certain changes and modifications can be made within the scope of the claims. Accordingly, the described embodiments are to be considered as illustrative and not restrictive, and the scope of the claims is not to be limited to details given herein, but can be modified within the scope and equivalents of the claims. In the claims, elements do not imply any particular order of operation, unless explicitly stated in the claims.

Many variations, modifications, additions, and improvements can be made. Plural instances can be provided for components, operations or structures described herein as a single instance. Boundaries between various components, operations and data stores are somewhat arbitrary, and particular operations are illustrated in the context of specific illustrative configurations. Other allocations of functionality are envisioned and can fall within the scope of the disclosure(s). In general, structures and functionality presented as separate components in exemplary configurations can be implemented as a combined structure or component. Similarly, structures and functionality presented as a single component can be implemented as separate components. It will be apparent to those skilled in the art that various modifications and variations can be made in the method and system of the disclosed subject matter without departing from the spirit or scope of the disclosed subject matter. These and other variations, modifications, additions, and improvements can fall within the scope of the appended claim(s) and their equivalents.

As described above in connection with certain embodiments, certain components, e.g., the user computers 102 and the Optimal Animal Growth Application Server 112 can include a computer or computers, processor, network, mobile device, cluster, or other hardware to perform various functions. Moreover, certain elements of the disclosed subject matter can be embodied in computer readable code which can be stored on computer readable media and which when executed can cause a processor to perform certain functions described herein. In these embodiments, the computer and/or other hardware play a significant role in permitting the system and method to diagnose growth abnormalities in order to maintain optimal growth in animals. For example, the presence of the computers, processors, memory, storage, and networking hardware provides the ability to diagnose, assess, treat, and/or monitor animals in a more efficient manner. Moreover, the systems and methods disclosed herein cannot be accomplished with pen or paper, as such information is received over a network in electronic form.

Additionally, as described above in connection with certain embodiments, certain components can communicate with certain other components, for example via a network, e.g., the internet. To the extent not expressly stated above, the disclosed subject matter is intended to encompass both sides of any transaction, including transmitting and receiving. One of ordinary skill in the art will readily understand that, with regard to the features described above, if one component transmits, sends, or otherwise makes available to another component, the other component will receive or acquire, whether expressly stated or not.

The presently disclosed subject matter is not to be limited in scope by the specific embodiments herein. Indeed, various modifications of the disclosed subject matter in addition to those described herein will become apparent to those skilled in the art from the foregoing description and the accompanying figures. Such modifications are intended to fall within the scope of the appended claims.

What is claimed is:

1. A method of diagnosing growth abnormalities in order to maintain optimal growth in non-human animals, by one or more servers, comprising:
   receiving, from a user computer, one or more first biomarker inputs and one or more personalized biomarker inputs relating to a first animal, wherein the one or more first biomarker inputs are selected from a group of biomarkers including animal identification or approximate animal size, animal breed, sex, date of birth, age, weight, date of measurement, and a neutering status, wherein the one or more first biomarker inputs comprise at least the neutering status;
   comparing the one or more first biomarker inputs of the first animal to at least one predetermined reference biomarker input stored in a reference database in order to obtain relevant health trend information relating to the first animal, wherein the predetermined reference biomarker input includes related biomarker inputs of healthy animals of the same species or within the same growth period as the first animal;
   training, based on the reference database, a linear discriminant analysis model configured for predicting body condition scores;
   constructing one or more reference growth centile curves and using a first generalized additive model for location, shape, and scale (GAMLSS) based on a box-cox cole-green (BCCG) function and a second GAMLSS based on a box-cox power exponential (BCPE) function;
   generating, based on the neutering status, one or more adjusted reference growth centile curves for the one or more reference growth centile curves, respectively;
   executing the linear discrimant analysis model to predict a body condition score for the first animal from the one or more first biomarker inputs comprising at least the neutering status;
   transforming the relevant health trend information, the one or more adjusted reference growth centile curves, and the body condition score to an output assessment comprising whether the first animal is at risk for at least one growth abnormality;
   generating, responsive to determining that the first animal is at risk for at least one growth abnormality, a customized recommendation for lifestyle treatment options, wherein the first biomarker input determined to be above or below the predetermined reference biomarker input indicates an increased likelihood in growth abnormalities in the first animal, and wherein the lifestyle treatment options are selected from a plurality of lifestyle treatment options in part based on their respective effectiveness with respect to the first animal; and
   sending, to the user computer, instructions for presenting the customized recommendation, the one or more adjusted reference growth centile curves, and the relevant health trend information of the first animal.

2. The method of claim 1, wherein the transforming includes calculating a recommended growth weight of the first animal.

3. The method of claim 1, wherein the customized recommendation comprises an intervention step for correction of the growth abnormality, and wherein the method further comprises:
   adjusting the customized recommendation based on the one or more personalized biomarker inputs, wherein the adjusted recommendation includes a tailored intervention step based on the intervention step in the customized recommendation.

4. The method of claim 1, wherein the one or more personalized biomarker inputs of the first animal include previous laboratory test results, food and water consumption patterns, diet, exercise routine, bowel movement schedule, medical history, and preexisting conditions.

5. The method of claim 1, further comprising:
   calculating, based on the one or more first biomarker inputs of the first animal, the difference between the weight of the first animal and a recommended growth weight of an ideal animal of the same species in a similar growth stage as the first animal;
   determining if the difference is within about two centiles of the recommended growth weight; and
   sending, to the user computer, instructions for presenting a recommendation based on the determination, wherein the recommendation includes a tailored intervention step if the difference is not within about two centiles of the recommended growth weight.

6. The method of claim 1, further comprising:
   determining a body condition of the first animal based on the one or more first biomarker inputs; and
   sending, to the user computer, instructions for presenting the body condition of the first animal.

7. The method of claim 1, further comprising:
   determining a projected growth potential of the first animal based on a comparison of the one or more first and personalized biomarker inputs and information stored in the reference database relating to the species or breed of the first animal; and
   sending, to the user computer, instructions for presenting the projected growth potential of the first animal.

8. The method of claim 1, wherein the relevant health trend information includes a growth curve and ideal body weight chart.

9. A computer system for diagnosing growth abnormalities in order to maintain optimal growth in non-human animals, comprising:
   a processor; and
   a memory storing instructions that, when executed by the processor, cause the computer system to:
      receive, from a user computer, one or more first biomarker inputs and one or more personalized biomarker inputs relating to a first animal, wherein the one or more first biomarker inputs are selected from a group of biomarkers including animal identification or approximate animal size, animal breed, sex, date of birth, age, weight, date of measurement, and a neutering status, wherein the one or more first biomarker inputs comprise at least the neutering status;
      compare the one or more first biomarker inputs of the first animal to at least one predetermined reference biomarker input stored in a reference database in order to obtain relevant health trend information relating to the first animal, wherein the predetermined reference biomarker input includes related biomarker inputs of healthy animals of the same species or within the same growth period as the first animal;

train, based on the reference database, a linear discriminant analysis model configured for predicting body condition scores;

construct one or more reference growth centile curves and using a first generalized additive model for location, shape, and scale (GAMLSS) based on a box-cox cole-green (BCCG) function and a second GAMLSS based on a box-cox power exponential (BCPE) function;

generate, based on the neutering status, one or more adjusted reference growth centile curves for the one or more reference growth centile curves, respectively;

execute the linear discrimant analysis model to predict a body condition score for the first animal from the one or more first biomarker inputs comprising at least the neutering status;

transform the relevant health trend information, the one or more adjusted reference growth centile curves, and the body condition score to an output assessment comprising whether the first animal is at risk for at least one growth abnormality;

generate, responsive to determining that the first animal is at risk for at least one growth abnormality, a customized recommendation for lifestyle treatment options, wherein the first biomarker input determined to be above or below the predetermined reference biomarker input indicates an increased likelihood in growth abnormalities in the first animal, and wherein the lifestyle treatment options are selected from a plurality of lifestyle treatment options in part based on their respective effectiveness with respect to the first animal; and send, to the user computer, instructions for presenting the customized recommendation, the one or more adjusted reference growth centile curves, and the relevant health trend information of the first animal.

10. The computer system of claim 9, wherein the transforming includes calculating a recommended growth weight of the first animal.

11. The computer system of claim 9, wherein the customized recommendation comprises an intervention step for correction of the growth abnormality, and wherein the instructions stored by the memory, when executed by the processor, further cause the computer system to:

adjust the customized recommendation based on the one or more personalized biomarker inputs, wherein the adjusted recommendation includes a tailored intervention step based on the intervention step in the customized recommendation.

12. The computer system of claim 9, wherein the one or more personalized biomarker inputs of the first animal include previous laboratory test results, food and water consumption patterns, diet, exercise routine, bowel movement schedule, medical history, and preexisting conditions.

13. The computer system of claim 9, wherein the instructions stored by the memory, when executed by the processor, further cause the computer system to:

calculate, based on the one or more first biomarker inputs of the first animal, the difference between the weight of the first animal and a recommended growth weight of an ideal animal of the same species in a similar growth stage as the first animal;

determine if the difference is within about two centiles of the recommended growth weight; and send, to the user computer, instructions for presenting a recommendation a recommendation on the graphical user interface based on the determination, wherein the recommendation includes a tailored intervention step if the difference is not within about two centiles of the recommended growth weight.

14. The computer system of claim 9, wherein the instructions stored by the memory, when executed by the processor, further cause the computer system to:

determine a body condition of the first animal based on the one or more first biomarker inputs; and send, to the user computer, instructions for presenting the body condition of the first animal.

15. The computer system of claim 9, wherein the instructions stored by the memory, when executed by the processor, further cause the computer system to:

determine a projected growth potential of the first animal based on a comparison of the one or more first and personalized biomarker inputs and information stored in the reference database relating to the species or breed of the first animal; and send, to the user computer, instructions for presenting the projected growth potential of the first animal.

16. The computer system of claim 9, wherein the relevant health trend information includes a growth curve and ideal body weight chart.

17. A non-transitory computer-readable medium storing instructions that, when executed by a processor, cause a computer system to diagnose growth abnormalities in order to maintain optimal growth in non-human animals, by performing the steps of:

receiving, from a user computer, one or more first biomarker inputs and one or more personalized biomarker inputs relating to a first animal, wherein the one or more first biomarker inputs are selected from a group of biomarkers including animal identification or approximate animal size, animal breed, sex, date of birth, age, weight, date of measurement, and a neutering status, wherein the one or more first biomarker inputs comprise at least the neutering status;

comparing the one or more first biomarker inputs of the first animal to at least one predetermined reference biomarker input stored in a reference database in order to obtain relevant health trend information relating to the first animal, wherein the predetermined reference biomarker input includes related biomarker inputs of healthy animals of the same species or within the same growth period as the first animal;

training, based on the reference database, a linear discriminant analysis model configured for predicting body condition scores;

constructing one or more reference growth centile curves and using a first generalized additive model for location, shape, and scale (GAMLSS) based on a box-cox cole-green (BCCG) function and a second GAMLSS based on a box-cox power exponential (BCPE) function;

generating, based on the neutering status, one or more adjusted reference growth centile curves for the one or more reference growth centile curves, respectively;

executing the linear discrimant analysis model to predict a body condition score for the first animal from the one or more first biomarker inputs comprising at least the neutering status;

transforming the relevant health trend information, the one or more adjusted reference growth centile curves, and the body condition score to an output assessment comprising whether the first animal is at risk for at least one growth abnormality;

generating, responsive to determining that the first animal is at risk for at least one growth abnormality, a customized recommendation for lifestyle treatment options, wherein the first biomarker input determined to be above or below the predetermined reference biomarker input indicates an increased likelihood in growth abnormalities in the first animal, and wherein the lifestyle treatment options are selected from a plurality of lifestyle treatment options in part based on their respective effectiveness with respect to the first animal; and sending, to the user computer, instructions for presenting the customized recommendation, the one or more adjusted reference growth centile curves, and the relevant health trend information of the first animal.

18. The non-transitory computer-readable medium of claim 17, wherein the transforming includes calculating a recommended growth weight of the first animal.

19. The non-transitory computer-readable medium of claim 17, wherein the customized recommendation comprises an intervention step for correction of the growth abnormality, and wherein the steps further comprise:

adjusting the customized recommendation based on the one or more personalized biomarker inputs, wherein the adjusted recommendation includes a tailored intervention step based on the intervention step in the customized recommendation.

20. The non-transitory computer-readable medium of claim 17, wherein the one or more personalized biomarker inputs of the first animal include previous laboratory test results, food and water consumption patterns, diet, exercise routine, bowel movement schedule, medical history, and preexisting conditions.

21. The non-transitory computer-readable medium of claim 17, further comprising:

calculating, based on the one or more first biomarker inputs of the first animal, the difference between the weight of the first animal and a recommended growth weight of an ideal animal of the same species in a similar growth stage as the first animal;

determining if the difference is within about two centiles of the recommended growth weight; and sending, to the user computer, instructions for presenting a recommendation based on the determination, wherein the recommendation includes a tailored intervention step if the difference is not within about two centiles of the recommended growth weight.

22. The non-transitory computer-readable medium of claim 17, further comprising:

determining a body condition of the first animal based on the one or more first biomarker inputs; and sending, to the user computer, instructions for presenting the body condition of the first animal.

23. The non-transitory computer-readable medium of claim 17, further comprising:

determining a projected growth potential of the first animal based on a comparison of the one or more first and personalized biomarker inputs and information stored in the reference database relating to the species or breed of the first animal; and sending, to the user computer, instructions for presenting the projected growth potential of the first animal.

24. The non-transitory computer-readable medium of claim 17, wherein the relevant health trend information includes a growth curve and ideal body weight chart.

* * * * *